(12) United States Patent
Gomi et al.

(10) Patent No.: US 9,338,379 B2
(45) Date of Patent: May 10, 2016

(54) SYSTEM, DEVICE, AND METHOD FOR OBTAINING AN IMAGE OF A PERSON'S SKIN

(71) Applicant: Sony Corporation, Tokyo (JP)

(72) Inventors: Shinichiro Gomi, Tokyo (JP); Masaru Suzuki, Tokyo (JP); Yusuke Nakamura, Chiba (JP)

(73) Assignee: Sony Corporation (JP)

( * ) Notice: Subject to any disclaimer, the term of this patent is extended or adjusted under 35 U.S.C. 154(b) by 408 days.

(21) Appl. No.: 13/845,763

(22) Filed: Mar. 18, 2013

(65) Prior Publication Data

US 2013/0256505 A1   Oct. 3, 2013

(30) Foreign Application Priority Data

Mar. 28, 2012   (JP) ................................ 2012-073536

(51) Int. Cl.
*H04N 5/369* (2011.01)
*H04N 5/232* (2006.01)
*H04N 5/235* (2006.01)
*A61B 5/00* (2006.01)

(52) U.S. Cl.
CPC .............. *H04N 5/369* (2013.01); *A61B 5/0077* (2013.01); *A61B 5/442* (2013.01); *H04N 5/2354* (2013.01); *H04N 5/23212* (2013.01)

(58) Field of Classification Search
CPC ...................................................... H04N 5/369
USPC ........................................ 250/201.4; 362/284
See application file for complete search history.

(56) References Cited

U.S. PATENT DOCUMENTS

| 5,580,163 | A | * | 12/1996 | Johnson, II | ................... | 362/285 |
| 6,614,596 | B2 | * | 9/2003 | Gladnick | ...................... | 359/630 |
| 2004/0008333 | A1 | * | 1/2004 | Oda et al. | ........................ | 355/55 |

FOREIGN PATENT DOCUMENTS

JP            06-105826 A        4/1994

* cited by examiner

*Primary Examiner* — Seung C Sohn
(74) *Attorney, Agent, or Firm* — Lerner, David, Littenberg, Krumholz & Mentlik, LLP

(57) ABSTRACT

There is provided an imaging device including a lighting unit whose lighting directions to a subject are able to be switched, and a control unit that performs focus adjustment on the subject for every lighting directions to calculate evaluation values in accordance with focus states, and determines a direction in which a focus state becomes best as a lighting direction based on the evaluation values to capture the subject.

13 Claims, 43 Drawing Sheets

FIG. 7
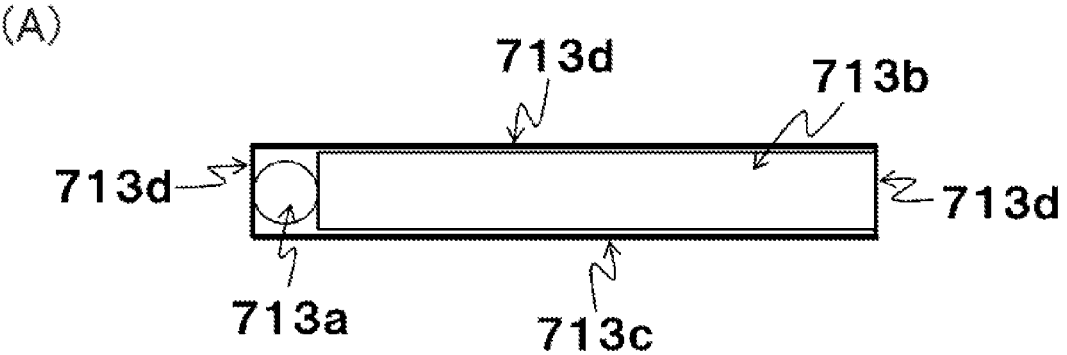
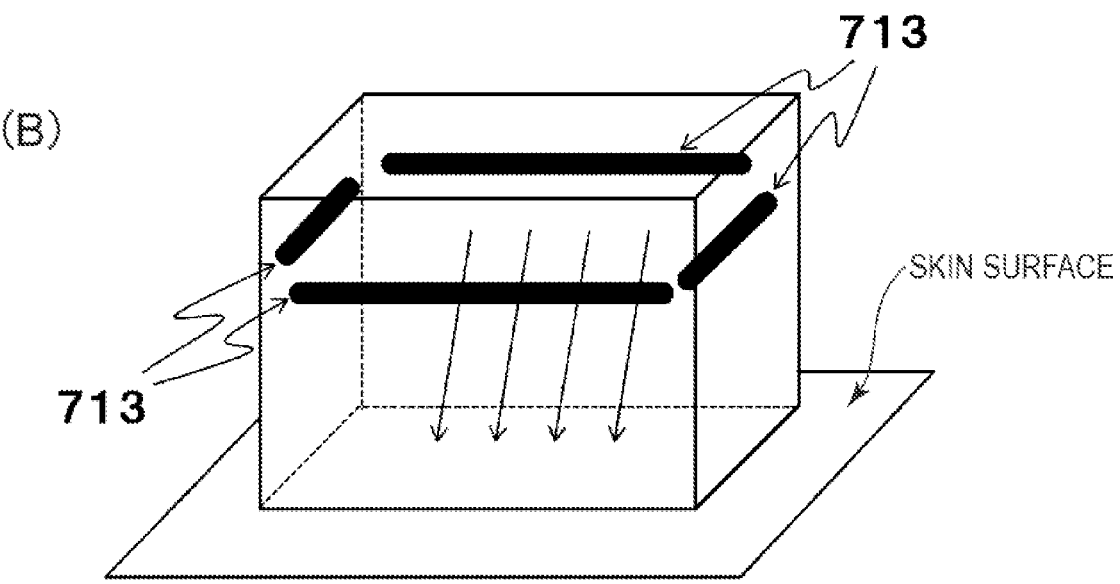

SYSTEM, DEVICE, AND METHOD FOR OBTAINING AN IMAGE OF A PERSON'S SKIN

CROSS-REFERENCE TO RELATED APPLICATION

The present application claims priority from Japanese Patent Application No. JP 2012-073536 filed in the Japanese Patent Office on Mar. 28, 2012, the entire content of which is incorporated herein by reference.

BACKGROUND

The present technology relates to an imaging device, an imaging method, a program, an imaging system, and an attachment device, and enables easy obtainment of a good skin image.

Conventionally, in the beauty industry and the like, and imaging device is used to capture skin, and a skin condition is analyzed based on the obtained skin image. For example, in JP H6-105826A, skin is captured while lighting is provided in a plurality of directions in sequence, and a three-dimensional shape of the surface of skin is restored from obtained image signals, so that more accurate features of the skin surface shape are extracted to conduct an analysis.

SUMMARY

When the analysis of a skin condition and the like are conducted, it is not possible to accurately conduct the analysis unless a clear skin image is used. However, in an imaging device used for readily and readily checking a skin condition and the like in a storefront and the like, the imaging device generally has a fixed focus, or it is necessary for a skilled clerk and the like to manually set the focus. For this reason, it is difficult for a general user to photograph a skin image suitable for analysis.

Thus, the present technology is directed to provide an imaging device, an imaging method, a program, an imaging system, and an attachment device capable of readily obtaining a good skin image.

According to a first embodiment of the present disclosure, there is provided an imaging device including a lighting unit whose lighting directions to a subject are able to be switched, and a control unit that performs focus adjustment on the subject for every lighting directions to calculate evaluation values in accordance with focus states, and determines a direction in which a focus state becomes best as a lighting direction based on the evaluation values to capture the subject.

According to the embodiment, a lighting unit may be configured so that its lighting directions to a subject are able to be switched. For example, the lighting unit switches the lighting directions by emitting illumination light from different positions in a circumferential direction with respect to an optical axis of an imaging optical system. The lighting unit may switch irradiation angles of the illumination light. The lighting unit may provide lighting using a light source having an emission wavelength suitable for an analysis process performed using a captured image of the subject. Further, the lighting unit may switch the lighting directions by switching light sources emitting illumination light, or controlling passage of illumination light emitted from a light source using a shutter.

A control unit may perform focus adjustment on the subject for every lighting directions to calculate evaluation values in accordance with focus states, and may determine a direction in which a focus state becomes best as a lighting direction based on the evaluation values to capture the subject. The control unit may thin out the lighting directions in the circumferential direction, perform focus adjustment on the subject for every lighting directions after thinning out to calculate evaluation values in accordance with focus states, and calculate evaluation values of the thinned-out lighting directions from the calculated evaluation values. Or, the control unit may group the lighting directions in the circumferential direction, and perform focus adjustment on the subject for every lighting directions in one group to calculate evaluation values in accordance with focus states. Note that the control unit may include lighting directions crossing at right angles in the one group. Further, the control unit may move a focus position by a predetermined distance with respect to a focus adjustment position at which the focus state becomes best based on the evaluation values.

According to a second embodiment of the present disclosure, there is provided an imaging method including providing lighting to a subject in a manner that lighting directions are able to be switched, and performing focus adjustment on the subject for every lighting directions to calculate evaluation values in accordance with focus states, and determining a direction in which a focus state becomes best as a lighting direction based on the evaluation values to capture the subject.

According to a third embodiment of the present disclosure, there is provided a program causing a computer to control operation of an imaging device having a lighting unit whose lighting directions to a subject are able to be switched, and to carry out a procedure of performing focus adjustment on the subject for every lighting directions to calculate evaluation values in accordance with focus states, and determining a direction in which a focus state becomes best as a lighting direction based on the evaluation values to capture the subject.

In addition, a program according to the present technology is a program capable of being provided via a recording medium or a communication medium providing various programs and codes, for example, to a general purpose computer executable of these in a computer-readable format, for example, a recording medium such as an optical disk, a magnetic disk and a semiconductor memory, or a communication medium such as a network. Such a program realizes a computer performing processes according to the program, provided in a computer-readable format.

According to a fourth embodiment of the present disclosure, there is provided an imaging system including an imaging device that generates a captured image of a subject, and an analysis device that analyzes the subject using the captured image. The imaging device may be configured to use a light source suitable for analyzing the subject, and include a lighting unit whose lighting directions to the subject are able to be switched, and a control unit that performs focus adjustment on the subject for every lighting directions to calculate evaluation values in accordance with focus states, and determines a direction in which a focus state becomes best as a lighting direction based on the evaluation values to capture the subject.

According to a fifth embodiment of the present disclosure, there is provided an attachment device including a lighting unit whose lighting directions to a subject are able to be switched. The lighting unit may switch lighting directions according to an instruction from an external device, or automatically switches lighting directions and outputs information indicating a lighting direction to the external device.

According to a sixth embodiment of the present disclosure, there is provided an imaging device including a reference pattern unit that is installed in a manner that a reference pattern used in adjustment for capturing a subject is included in an imaging angle of view, and a control unit that captures the subject after adjustment for capturing the subject using the reference pattern.

According to a seventh embodiment of the present disclosure, there is provided an attachment device including a reference pattern unit that is installed in a manner that a reference pattern used in adjustment for capturing a subject is included in an imaging angle of view.

According to this technology, since lighting directions to a subject can be switched, focus adjustment is performed on a subject for every lighting directions to calculate evaluation values in accordance with focus states, and a direction in which a focus state becomes best is determined as a lighting direction based on the evaluation values to capture the subject. For this reason, lighting is provided in an optimal direction to perform focus adjustment, and it becomes possible to readily obtain a skin image whose focus state is good.

BRIEF DESCRIPTION OF THE DRAWINGS

FIG. 7 is a diagram illustrating a case in which a plurality of lighting modules are installed;

FIG. 27 is a diagram showing an example of a case in which there are body hairs and the like;

DETAILED DESCRIPTION OF THE EMBODIMENT(S)

Figure 1:
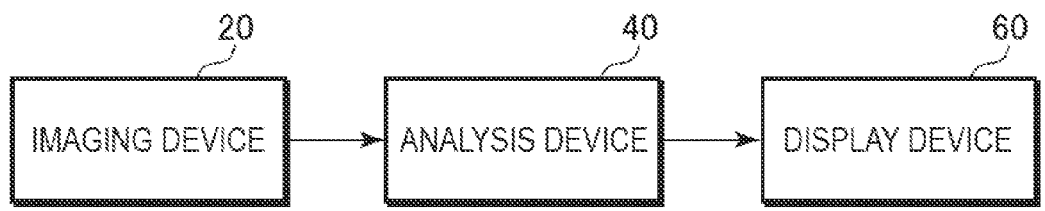
FIG. 1 is a diagram showing an example of a configuration of a skin condition analysis system.

Hereinafter, preferred embodiments of the present technology will be described in detail with reference to the appended drawings. Note that, in this specification and the appended drawings, structural elements that have substantially the same function and structure are denoted with the same reference numerals, and repeated explanation of these structural elements is omitted.

Hereinafter, modes for carrying out will be described. Description will be made in the following order.

1. Regarding Skin Analysis System
2. First Embodiment
2-1. Regarding Imaging Device
2-1-1. Configuration of Imaging Device
2-1-2. Operation of Imaging Device
2-1-3. Another Configuration of Attachment Device
2-1-4. Focus Operation of Imaging Device
2-2. Regarding Analysis Device
2-3. Regarding Display Device
3. Second Embodiment
3-1. Configuration of Imaging Device
3-2. Operation of Imaging Device
3-3. Another Configuration of Attachment Device
3-4. Regarding Image Processing Device and Display Device 1. Regarding Skin Analysis System FIG. 1 shows an example of a configuration of a skin condition analysis system. A skin condition analysis system 10 has a configuration including an imaging device 20, an analysis device 40, and a display device 60. The imaging device 20 switches lighting directions to perform focus adjustment for every directions, thereby determining an optimal focus position. Also, the imaging device 20 outputs an image signal of a skin image obtained by carrying out photography at the determined optimal focus position to the analysis device 40. The analysis device 40 performs analysis of a skin condition and the like based on the image signal of the skin image supplied from the imaging device 20, generates a display signal indicating the analysis results, and outputs the display signal to the display device 60. The display device 60 performs image display based on the display signal supplied from the analysis device 40, thereby displaying the analysis results of the skin condition and the like on a screen.

Figure 2:
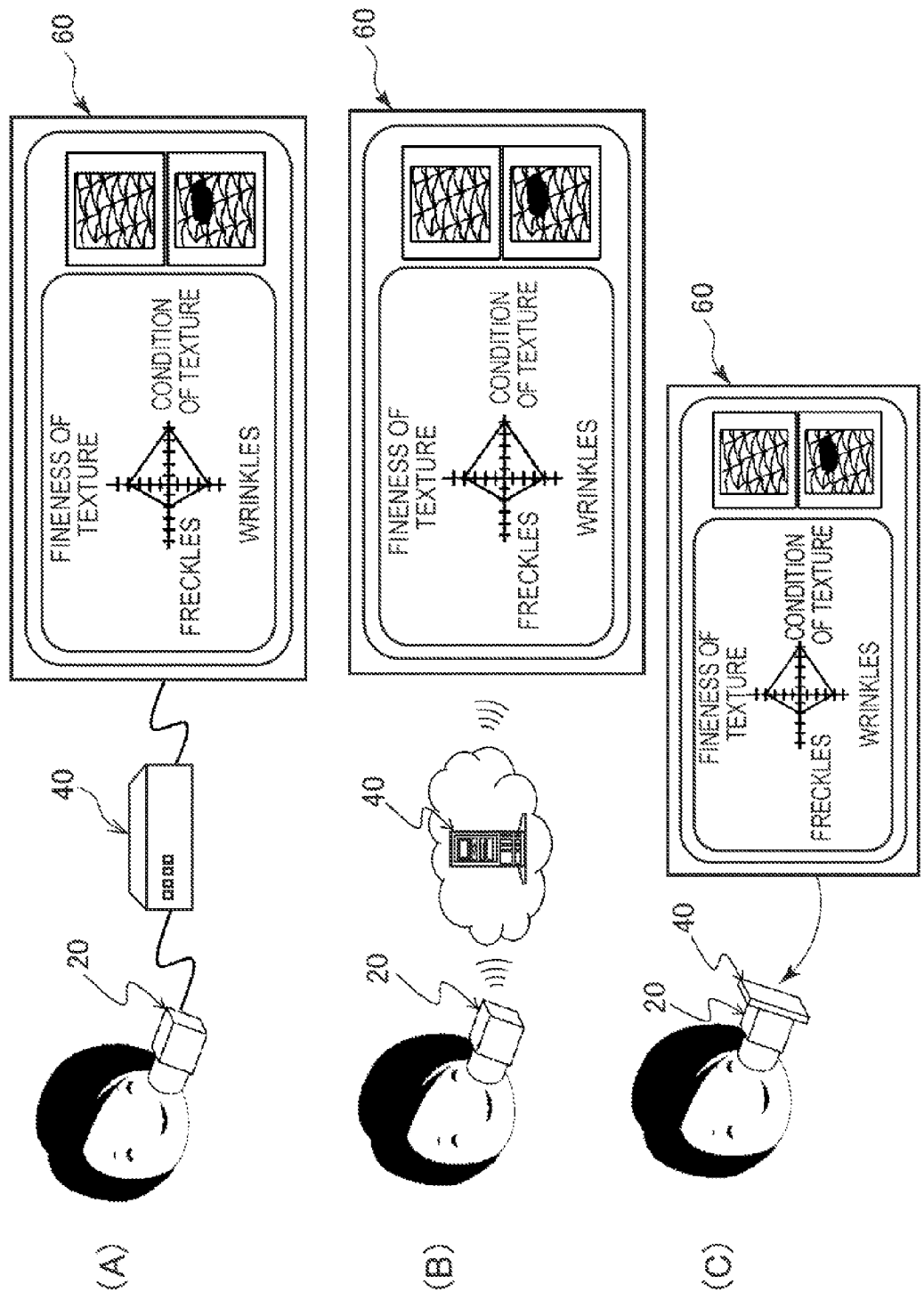
FIG. 2 is a diagram showing examples of a connection state between an imaging device, an analysis device, and a display device.

FIG. 2 shows examples of a connection state between the imaging device 20, the analysis device 40, and the display device 60. For example, as shown in FIG. 2(A), the imaging device 20 and the analysis device 40, and the analysis device and the display device 60 are connected through wired transmission paths. Also, as shown in FIG. 2(B), the imaging device 20 and the analysis device 40, and the analysis device 40 and the display device 60 may be configured to be connected through wireless transmission paths. Furthermore, as shown in FIG. 2(C), the imaging device 20 and the analysis device 40 may be integrally configured. Although not shown in the drawing, the analysis device 40 and the display device 60 may be integrally configured, or the imaging device 20, the analysis device 40 and the display device 60 may be integrally configured.

Figure 3:
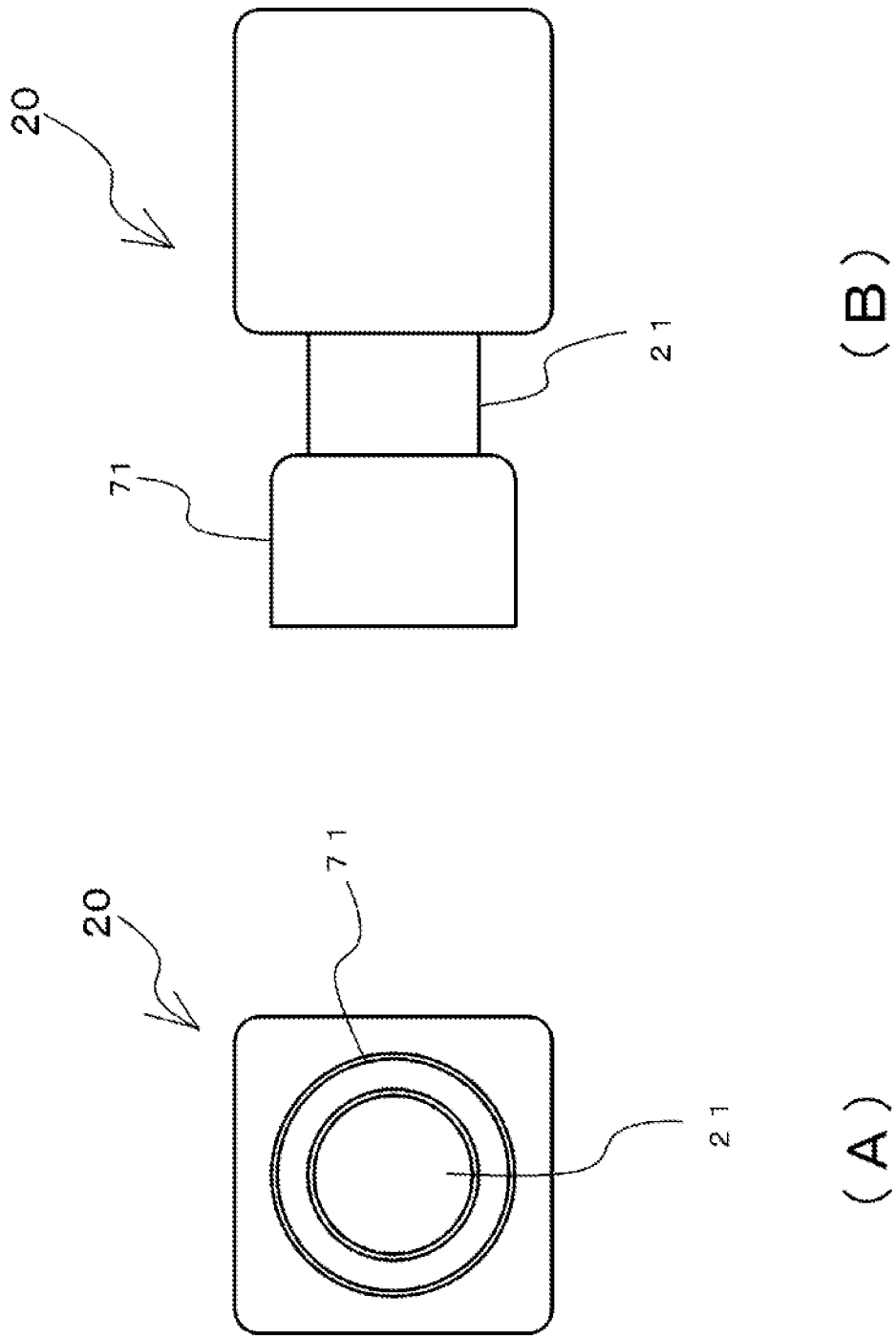
FIG. 3 is a diagram schematically showing an outer appearance of an imaging device.

2. First Embodiment 2-1. Regarding Imaging Device
2-1-1. Configuration of Imaging Device The imaging device 20 is configured so that it is possible to switch lighting directions and capture skin. FIG. 3 schematically shows an outer appearance of the imaging device 20. Here, FIG. 3(A) is a front view of the imaging device 20, and FIG. 3(B) is a side view of the imaging device 20. On the front end of a camera cone 21 of the imaging device 20, an attachment device 71 is installed. The attachment device 71 may be integrally configured with the camera cone 21, or may be configured to be attachable to and detachable from the camera cone 21.

Figure 4:
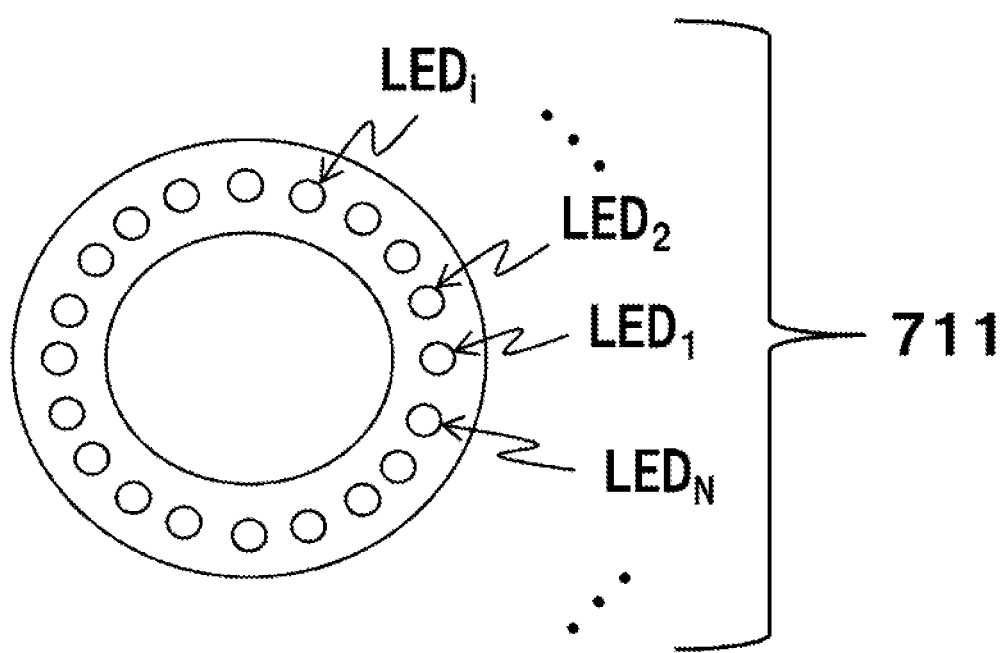
FIG. 4 is a diagram showing examples of light sources installed in an attachment device.

The attachment device 71 has a lighting unit whose lighting directions to a subject can be switched. For example, on the front end of the attachment device 71, a plurality of light sources 711 (for example, LED (Light Emitting Diode) 1 to LEDn) constituting the lighting unit are arranged in a ring shape as shown in FIG. 4, and are configured so that a lighting direction to a skin surface which is a subject can be changed by switching light sources that are caused to emit light. A wavelength band of a light source may be a visible region (400 to 700 nm), and an image sensor that will be described later may be a general image sensor that has spectral sensitivity in the visible region, for example, an image sensor that employs a filter of three primary colors of RGB.

Figure 5:
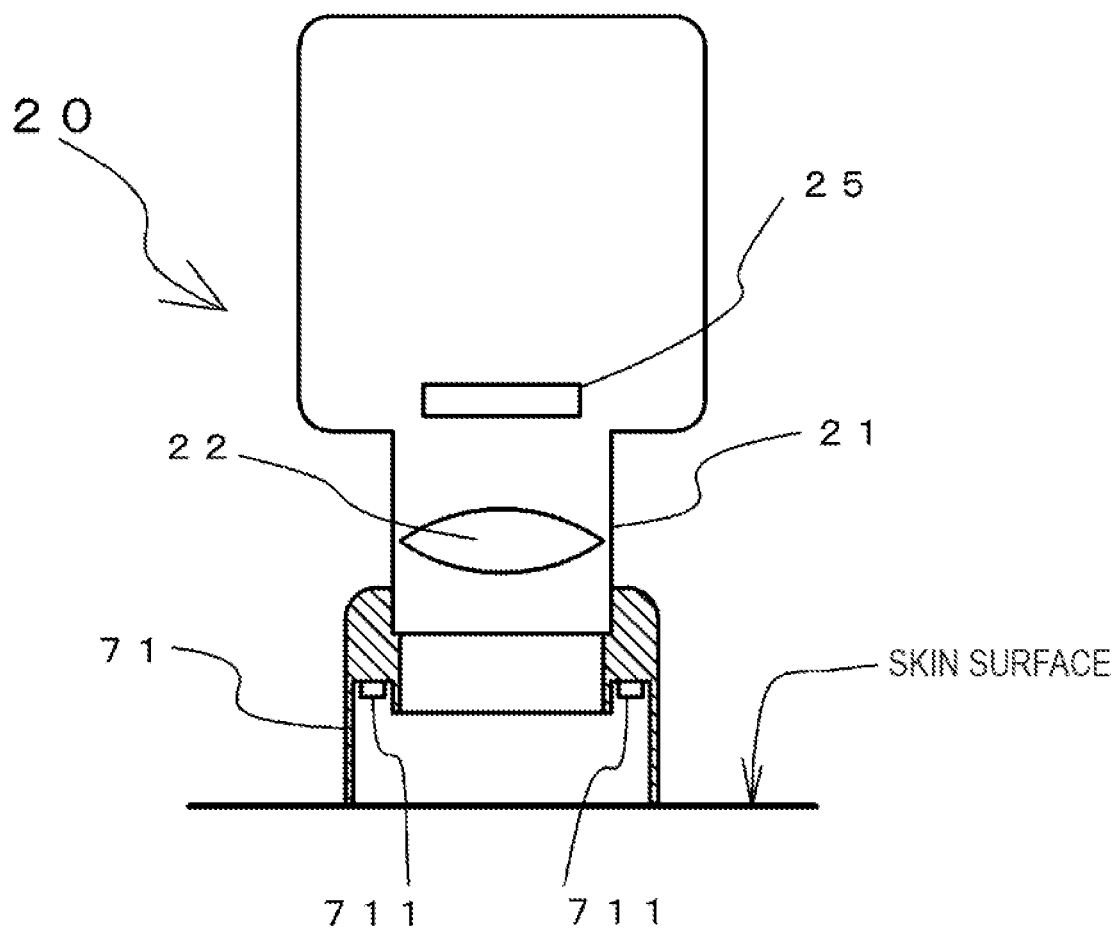
FIG. 5 is a diagram schematically showing an internal configuration of an imaging device.

FIG. 5 schematically shows an internal configuration of the imaging device 20. In the camera cone 21, an imaging optical system 22 and an image sensor 25 are installed.

Although FIG. 4 shows a case in which a lighting unit is configured by arranging a plurality of light sources toward a subject side in a ring shape on the front end side of a camera cone, the lighting unit is not limited to the configuration shown in FIG. 4. Next, an example of another configuration of the lighting unit will be shown.

Figure 6:
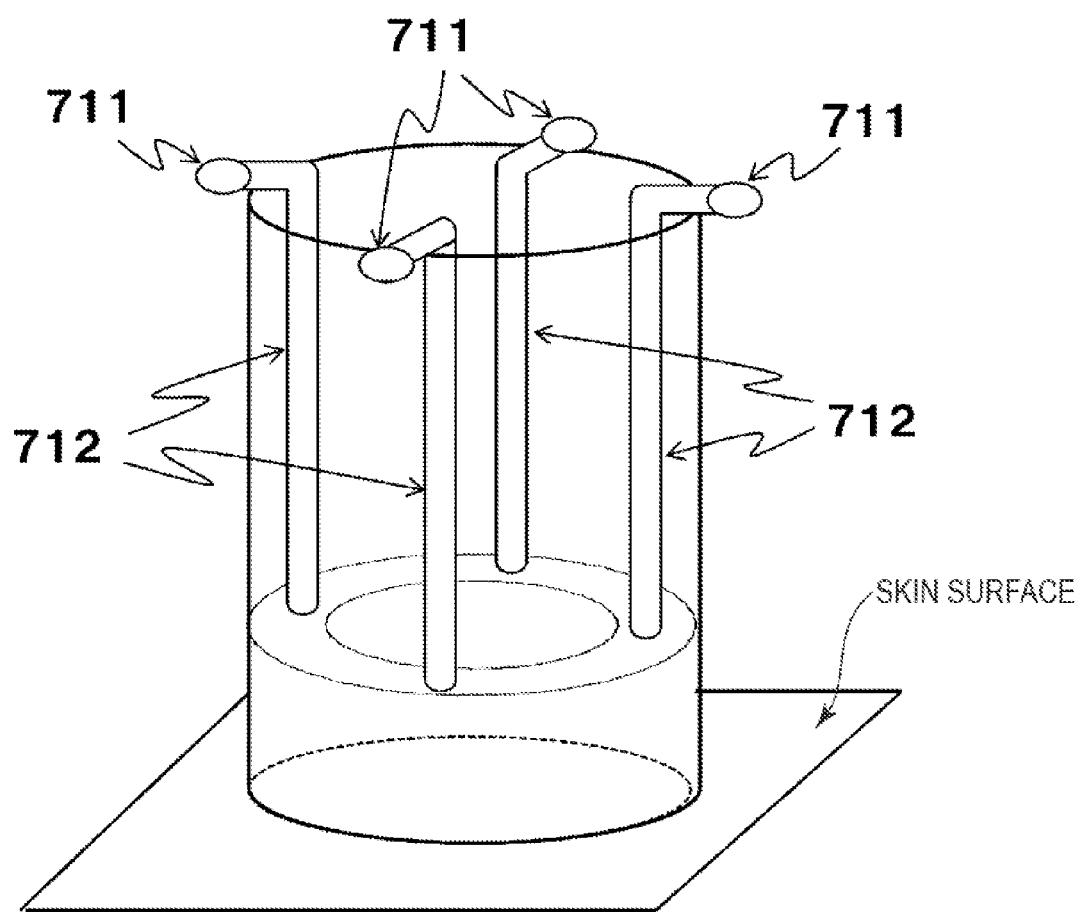
FIG. 6 is a diagram showing an example of another configuration of light sources.

FIG. 6 shows a case in which illumination light emission positions and the plurality of light sources 711 are each coupled with optical fibers 712, and light emitted from the light sources 711 is output from the illumination light emission positions to a skin surface through the optical fibers 712. Also, FIG. 6 shows a case in which four light sources are installed. As describe above, by guiding illumination light from a light source using a light guide path such as an optical fiber, limitations of the size of the light sources 711 and the like are reduced, and it is possible to increase the degree of freedom in designing an attachment device.

FIG. 7 shows an example of a case in which a plurality of lighting modules are installed, and lighting directions to a skin surface are switched by switching modules that emit illumination light. As shown in FIG. 7(A), a light source 713a and a light guide plate 713b are installed in a case of a lighting module 713, and the light source 713a is installed at an end of the light guide plate 713b. A diffusion plate 713c is installed in an illumination light emission surface of the case, and a reflection plate 713d is installed in the other surface side.

Light emitted from the light source 713a is directly incident on the light guide plate 713b, or is reflected by the reflection plate 713d and incident on the light guide plate 713b. The light incident on the light guide plate 713b is reflected by the reflection plate 713d and incident again on the light guide plate 713b. Light emitted from an illumination light emission surface of the light guide plate 713b is diffused by the diffusion plate 713c and emitted from the lighting module 713.

FIG. 7(B) shows an example of the attachment device 71 in which a plurality of lighting modules 713 are installed. Illumination light emission surfaces of the plurality of lighting modules 713 used in the attachment device 71 are attached toward the direction of a skin surface. FIG. 7(B) shows an example of a case in which four lighting modules are employed.

As describe above, using the plurality of lighting modules 713, lighting modules 713 that emit illumination light are switched, and thereby a lighting direction to a skin surface can be changed.

Although, in the configuration described above, an example of a case in which a lighting direction to a skin surface is changed by switching light sources that emit illumination light has been shown, a change of a lighting direction is not limited to a switch of light sources but may be accomplished through another method. For example, passage of illumination light emitted from a light source may be controlled by a shutter, and thereby lighting directions may be switched.

Figure 8:
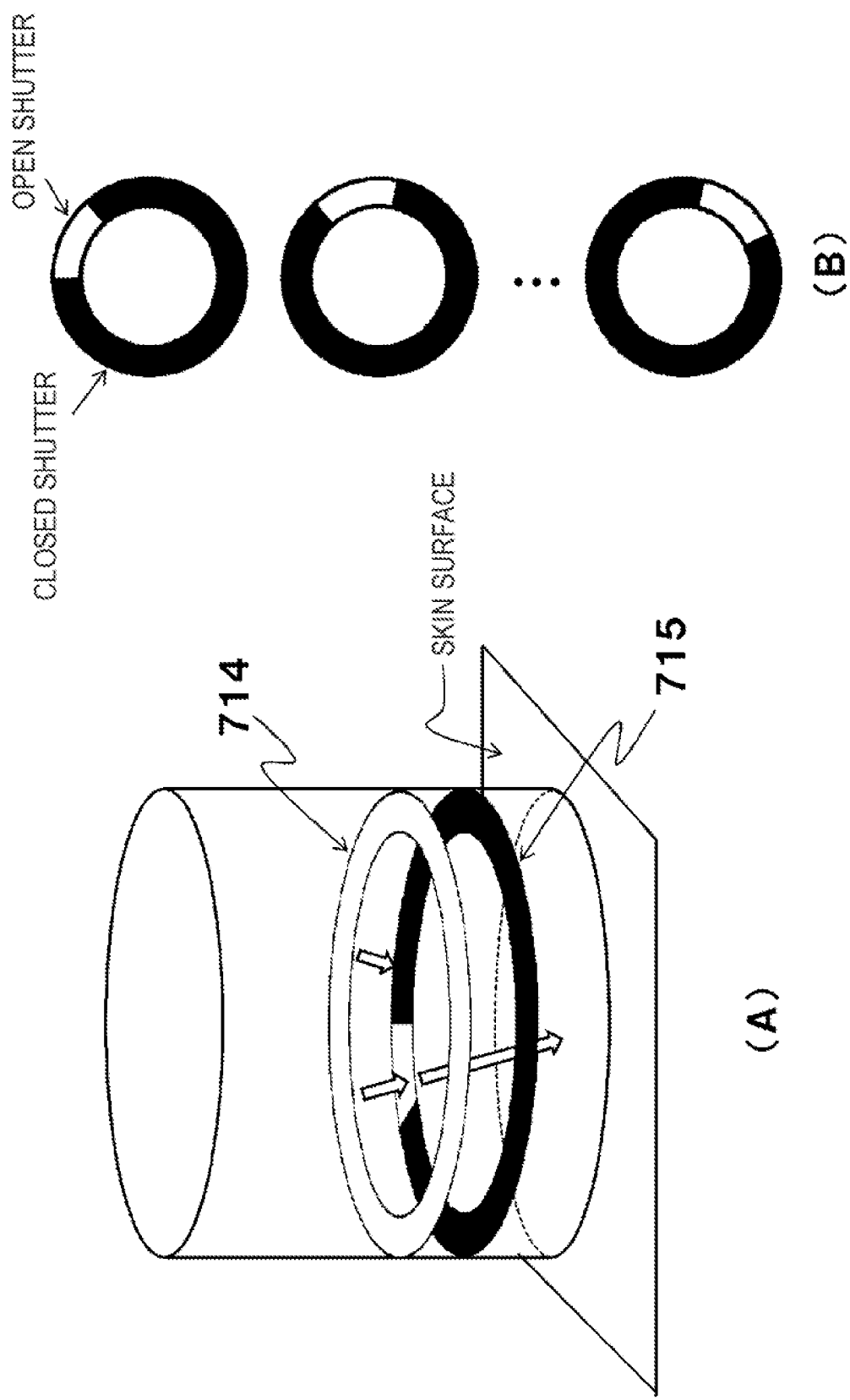
FIG. 8 is a diagram showing an example of a configuration of a case in which a lighting direction is changed by controlling passage of illumination light.

FIG. 8 shows an example of a configuration of a case in which a lighting direction is changed by controlling passage of illumination light. As shown in FIG. 8(A), the attachment device 71 has a ring light 714 and a shutter 715 having a ring shape. The ring light 714 emits illumination light toward the direction of a skin surface. The shutter 715 is installed on an illumination light emission side of the ring light 714. The shutter 715 is configured using, for example, liquid crystal elements, and configured to be able to control passage of illumination light for each of a plurality of divided regions. In the attachment device 71 configured in this way, a lighting direction is changed by moving a region (open shutter region) which enables illumination light to be passed as shown in FIG. 8(B).

As described above, the attachment device 71 switches light sources that are turned on or open shutter regions, that is, emits illumination light from a different position in a circumferential direction with reference to an optical axis of an imaging optical system, thereby switching lighting directions.

Here, when a level difference of a skin surface is small, it is possible to accurately detect depressions of the skin surface (wrinkles and the like) by controlling a lighting direction. However, when a level difference of a skin surface is large, there is a concern about a portion in which it is not possible to detect depressions of the skin surface even by controlling a lighting direction.

Figure 9:
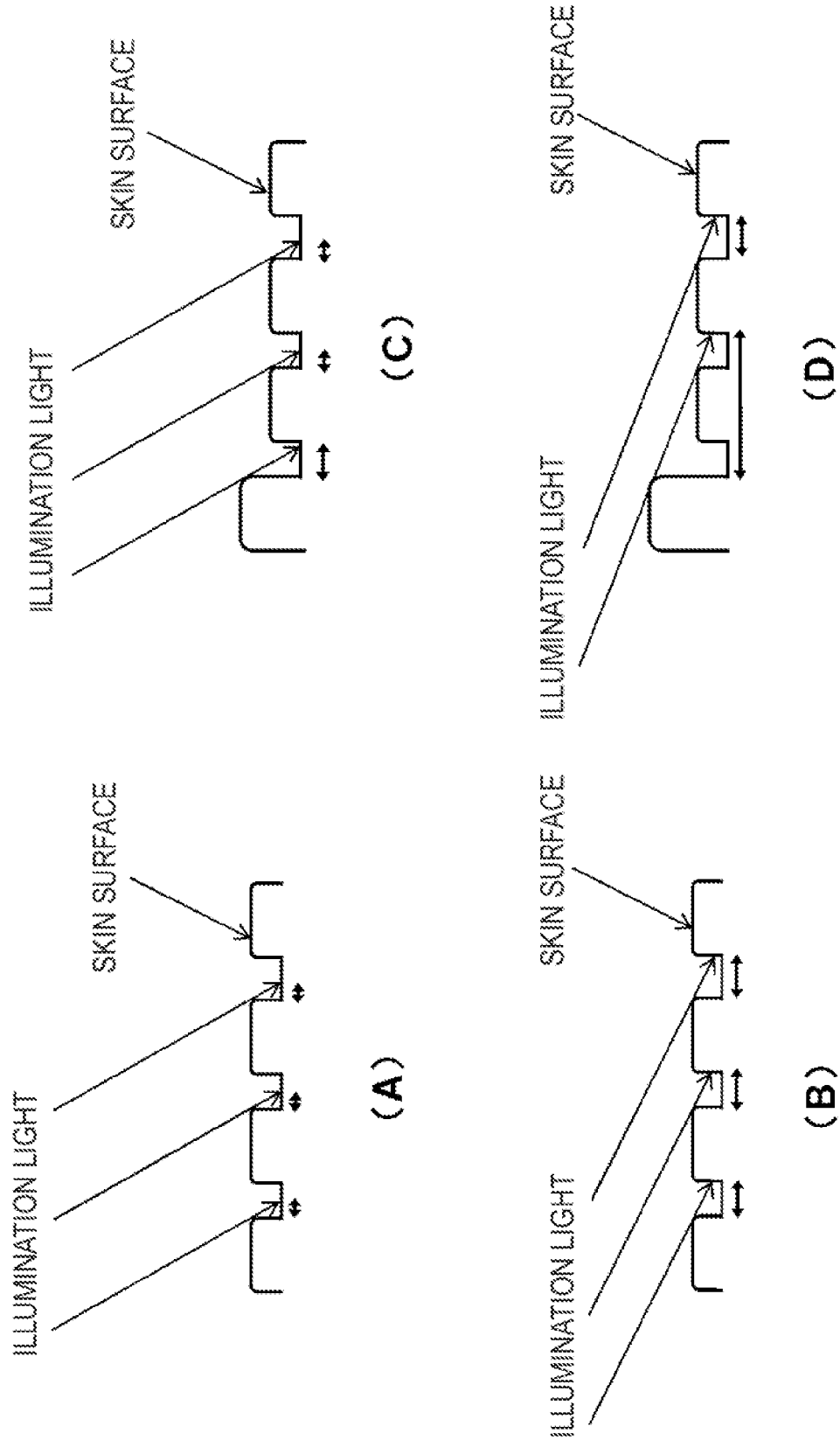
FIG. 9 is a diagram showing examples of a relationship between a condition of a skin surface and an irradiation angle of illumination light with respect to the skin surface.

FIG. 9 shows examples of a relationship between a condition of a skin surface and an irradiation angle of illumination light with respect to the skin surface. For example, FIG. 9(A) shows a case in which a level difference of a skin surface is small, and an irradiation angle of illumination light is large (when an output position of illumination light is high), and FIG. 9(B) shows a case in which a level difference of a skin surface is small, and an irradiation angle of illumination light is small (when an output position of illumination light is low). Also, FIG. 9(C) shows a case in which a level difference of a skin surface is large, and an irradiation angle of illumination light is large, and FIG. 9(D) shows a case in which a level difference of a skin surface is large, and an irradiation angle of illumination light is small.

As shown in FIGS. 9(A) and 9(B), when a level difference of a skin surface is small, a shadow (indicated by an arrow) is generated in a depressed portion of the skin surface, so that the depression of the skin surface can be accurately detected regardless of an irradiation angle of illumination light. As shown in FIG. 9(C), even if a level difference of a skin surface is large, when an irradiation angle of illumination light is large, a shadow (indicated by an arrow) is generated in a depressed portion of the skin surface, so that the depression of the skin surface can be accurately detected. However, as shown in FIG. 9(D), when a level difference of a skin surface is large, and an irradiation angle of illumination light is small, a depressed portion of the skin surface is hidden in a shadow (indicated by an arrow), and there is a concern that the depression of the skin surface becomes unable to be accurately detected. Thus, by enabling a switch of irradiation angles of illumination light, a change of a lighting direction may be enabled.

Figure 10:
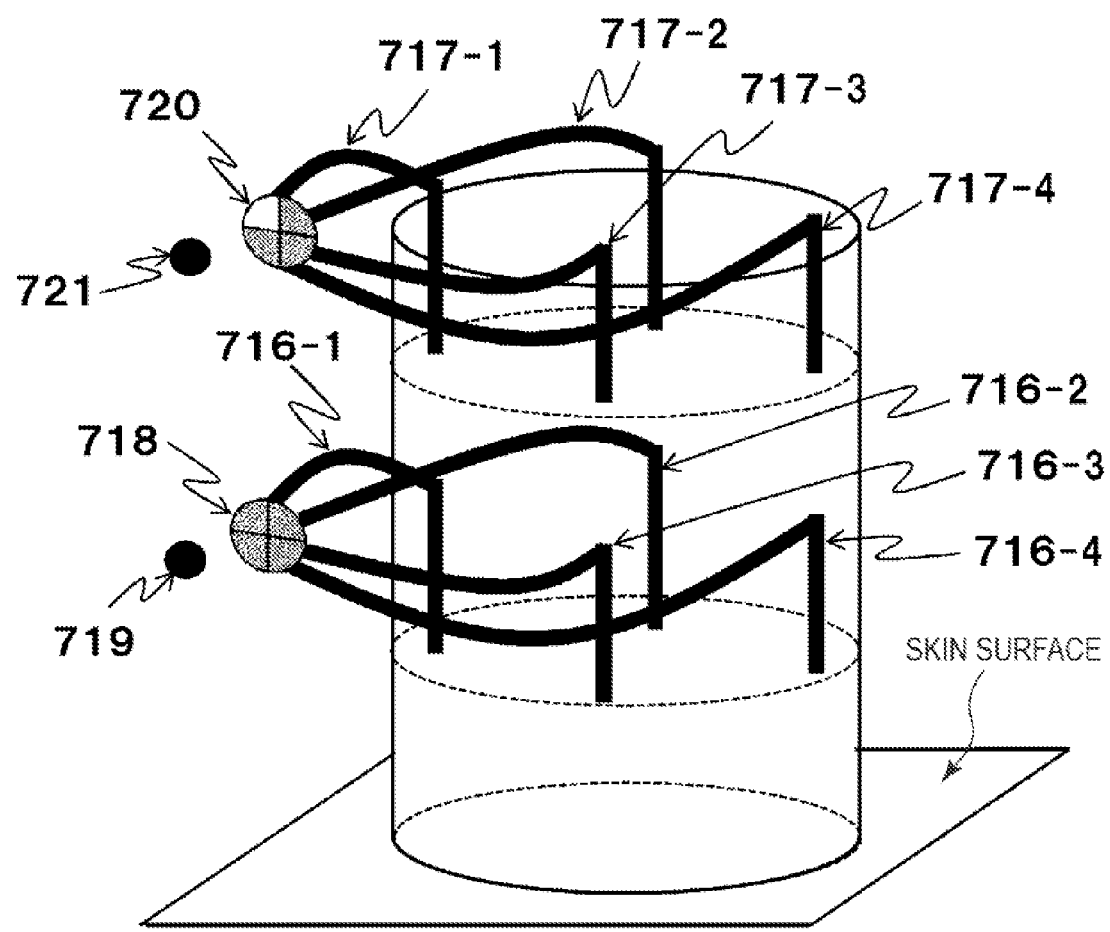
FIG. 10 is a diagram showing an example of a configuration of an attachment device when an output position of illumination light and a lighting direction are changed.

FIG. 10 shows an example of a configuration of the attachment device 71 when an output position and a lighting direction of illumination light are changed. Here, FIG. 10 shows a configuration in which an irradiation angle of illumination light can be changed in two stages, and a lighting direction can be changed with four directions.

The attachment device 71 has optical fibers 716-1 to 716-4 that output illumination light at first output positions, and optical fibers 717-1 to 717-4 that output illumination light at second output positions that are farther from a skin surface than the first output positions. On an opposite surface side of an illumination light emission surface of the optical fibers 716-1 to 716-4, a light source 719 is installed with a shutter 718 interposed therebetween. Also, on an opposite surface side of an illumination light emission surface of the optical fibers 717-1 to 717-4, a light source 721 is installed with a shutter 720 interposed therebetween. The attachment device 71 configured in this way outputs illumination light from, for example, the light source 719 toward the shutter 718. The shutter 718 controls incidence of the illumination light emitted from the light source 719 to the optical fibers 716-1 to 716-4 to decrease an irradiation angle of the illumination light, thereby switching lighting directions. Also, illumination light is output from the light source 721 toward the shutter 720. The shutter 720 controls incidence of the illumination light emitted from the light source 721 to the optical fibers 717-1 to 717-4 to increase an irradiation angle of the illumination light, thereby switching lighting directions. In this way, even when a level difference of a skin surface is large, it becomes possible to detect depressions of the skin surface. Also, by causing illumination light from a light source to be incident on respective optical fibers through a shutter that employs liquid crystals and the like, it becomes possible to concentrate switch portions of lighting to one spot. Accordingly, the shutter can be downsized. Also, it is possible to reduce a region and the like necessary for a control line for controlling operation of the shutter. Although FIG. 10 shows an example of a configuration in which optical fibers are employed, light sources may be installed at positions in illumination light emission surfaces of optical fibers, and an irradiation angle and a lighting direction of illumination light may be changed by switching light sources that output the illumination light.

Figure 11:
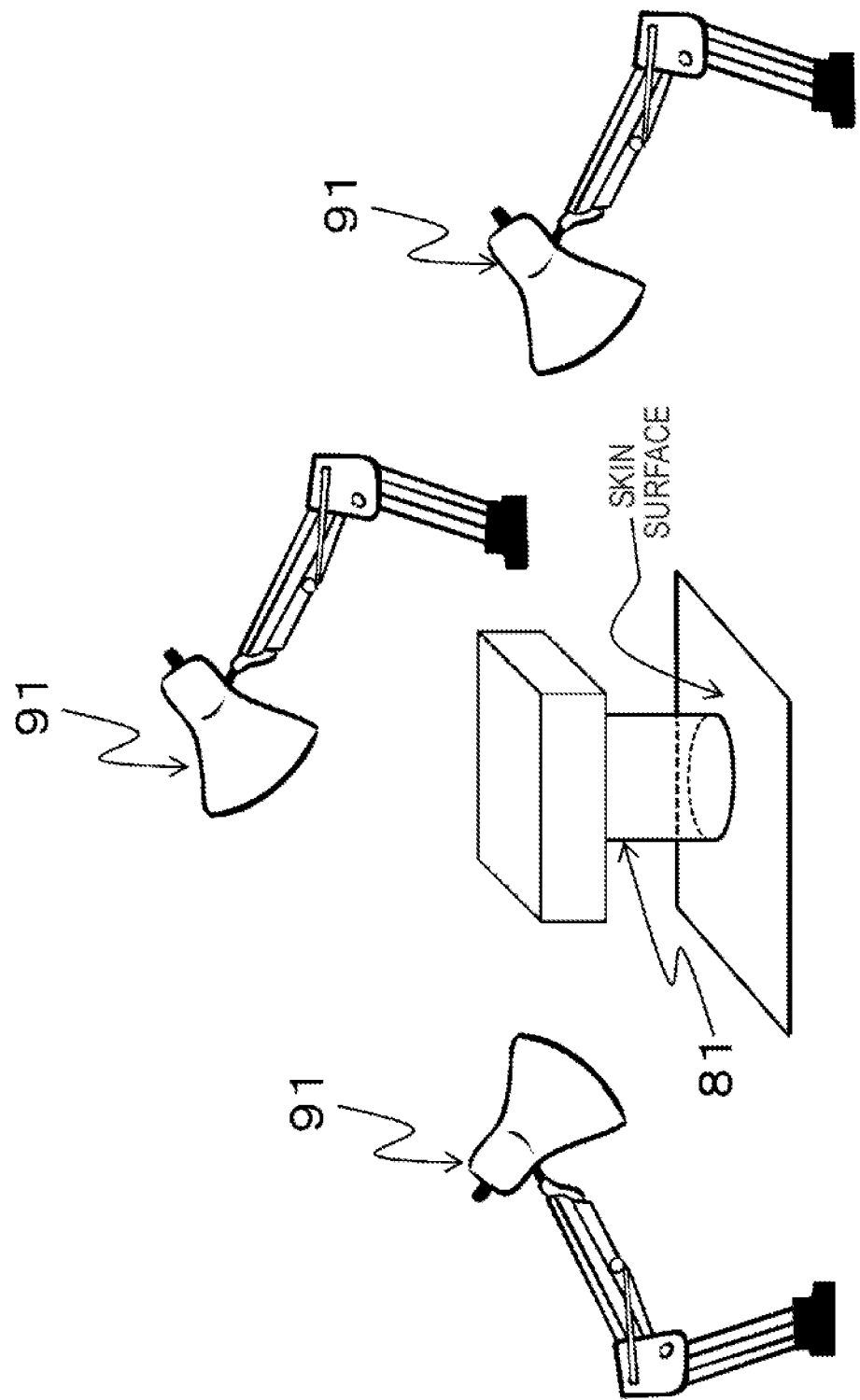
FIG. 11 is a diagram showing an example of a case in which illumination light is emitted from an external light source to a skin surface.
Figure 12:
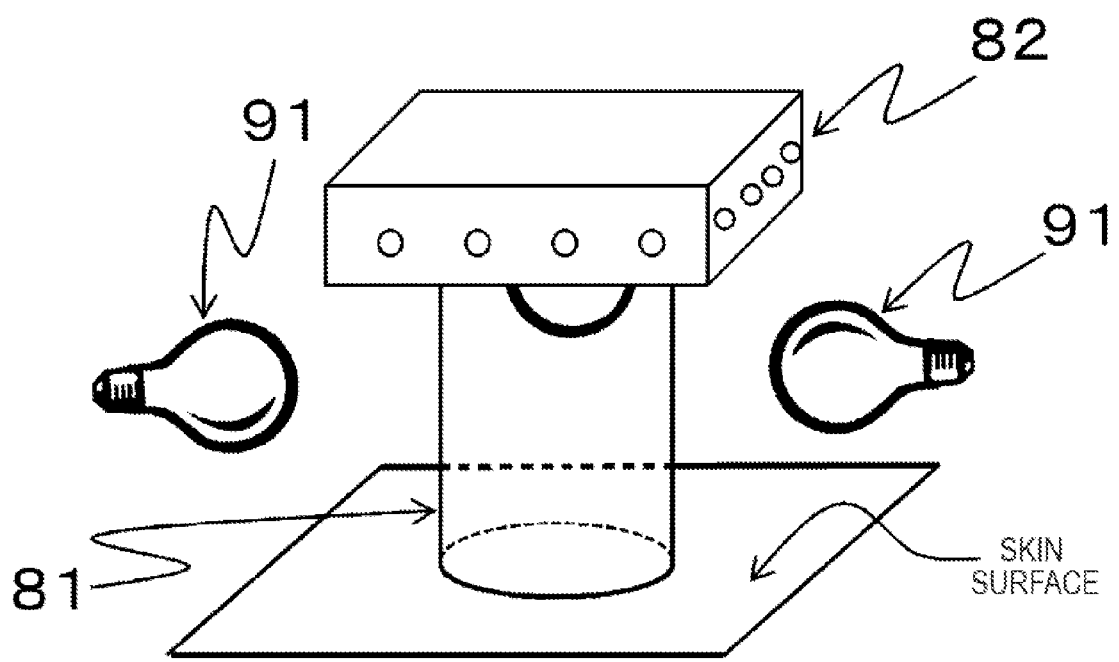
FIG. 12 is a diagram showing a case in which an indication display unit that indicates a lighting direction is installed.

In the imaging device 20, a transparent attachment component 81 may be installed on the front end of the camera cone 21, and as shown in FIG. 11, illumination light may be emitted from an external light source 91 to a skin surface. Also, as shown in FIG. 12, an indication display unit 82 that indicates a lighting direction may be installed on the attachment component 81 so as to be capable of determining a direction from which illumination light is emitted, and illumination light may be emitted from a direction indicated by the indication display unit 82 to a skin surface.

Figure 13:
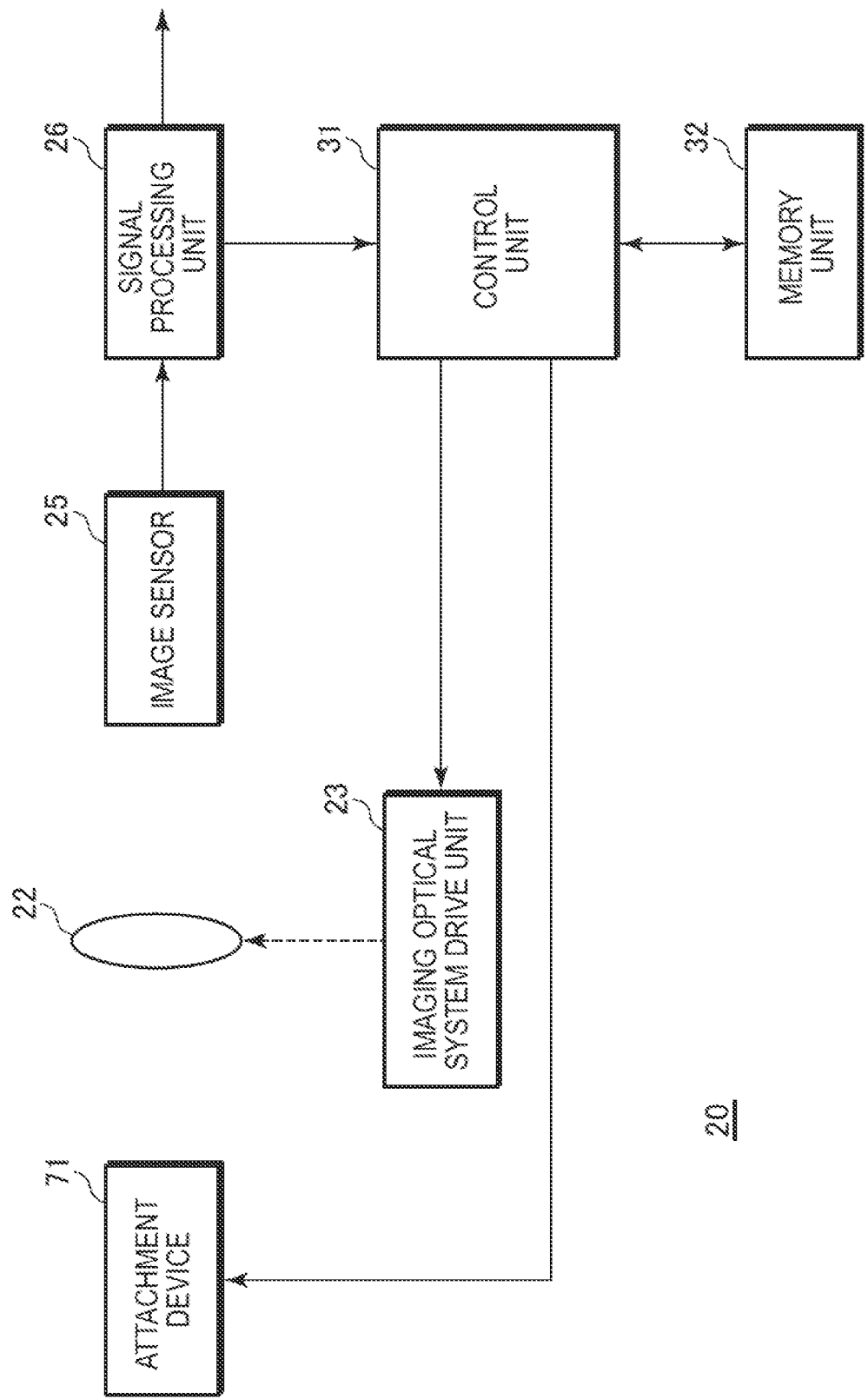
FIG. 13 is a block diagram showing a functional configuration of an imaging device.

FIG. 13 is a block diagram showing a functional configuration of the imaging device 20. The imaging device 20 has an imaging optical system 22, an imaging optical system drive unit 23, the image sensor 25, a signal processing unit 26, a control unit 31, a memory unit 32, and the attachment device 71.

The imaging optical system 22 is configured using a focus lens, a zoom lens, or the like, and forms an optical image of a subject on an imaging surface of the image sensor 25 in a desired size.

The imaging optical system drive unit 23 drives a focus lens or a zoom lens of the imaging optical system 22 based on a control signal from the control unit 31.

The image sensor 25 is configured using an imaging element such as a CMOS (Complementary Metal Oxide Semiconductor), a CCD (Charge Coupled Device), or the like. The image sensor 25 performs light source conversion, generates an image signal in accordance with the optical image of the subject, and outputs the image signal to the signal processing unit 26.

The signal processing unit 26 performs a variety of camera signal processes, for example, adjustment of brightness, color, or the like, a process for improving picture quality, and the like, on the image signal supplied from the image sensor 25, and outputs the processed image signal to the analysis device 40.

The control unit 31 controls operation of the image sensor 25 or the signal processing unit 26 and the attachment device 71, and generates an image signal of a skin image. In generation of the image signal of the skin image, the control unit 31 performs focus adjustment on a skin surface that is a subject for every lighting directions, and calculates evaluation values in accordance with focus states. The control unit 31 determines a direction in which a focus state becomes best as a lighting direction based on the calculated evaluation values to capture the subject.

The memory unit 32 stores information necessary for performing operation control of the imaging device 20 and the like. For example, the evaluation values for every lighting directions calculated by the control unit 31 are stored, so that the control unit 31 can capture in the optimal focus state based on the stored evaluation values.

The attachment device 71 performs a switch of lighting directions and the like according to an instruction from the control unit 31 of the imaging device 20 so that capturing can be performed in the optimal focus state or the like. Also, the attachment device 71 may be a configuration that automatically switches lighting directions and outputs information indicating a lighting direction to the control unit 31 of the imaging device 20.

2-1-2. Operation of Imaging Device

Figure 14:
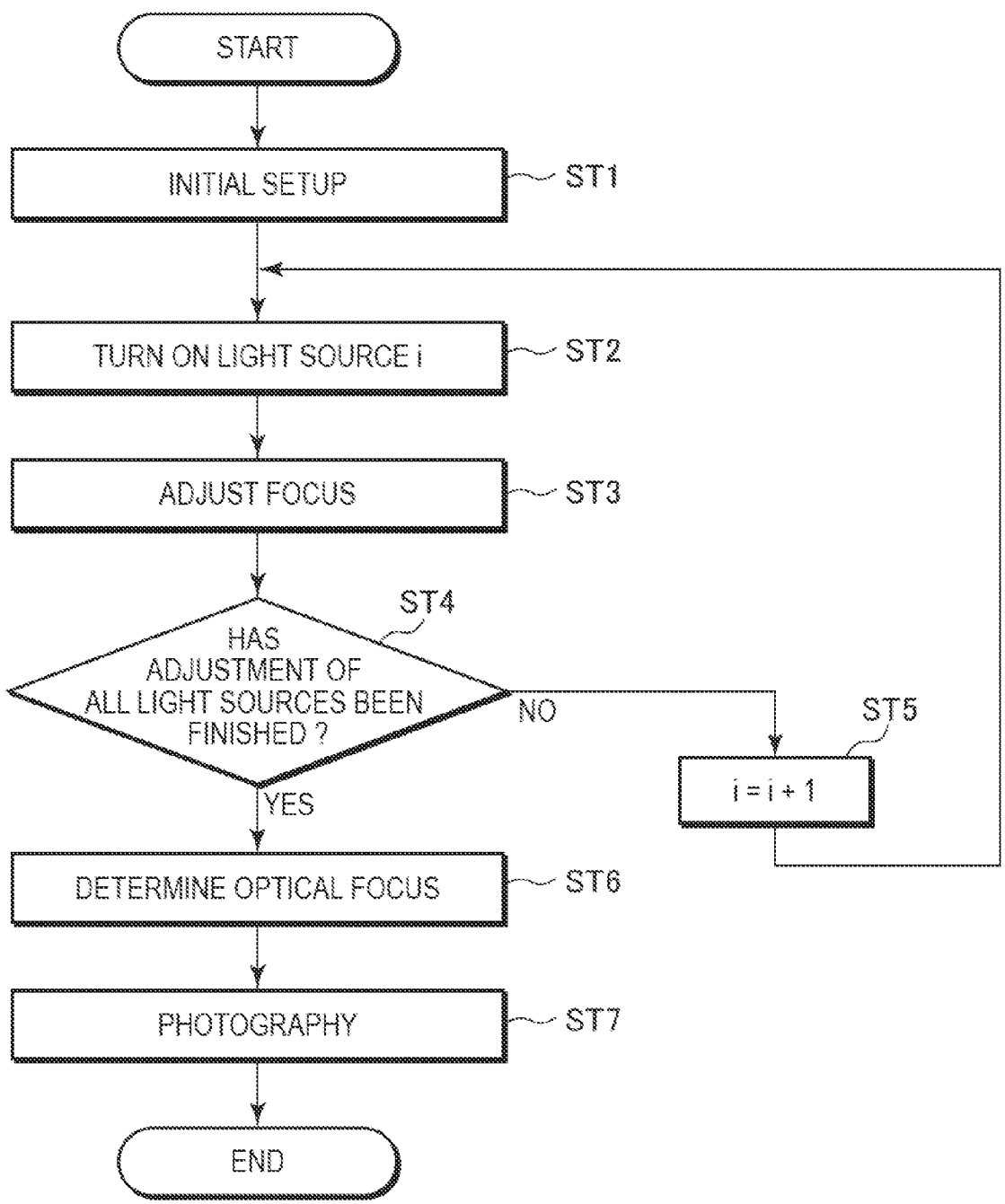
FIG. 14 is a flowchart illustrating operation of an imaging device.

Next, operation of an imaging device will be described. FIG. 14 is a flowchart illustrating operation of an imaging device. In step ST1, the imaging device 20 performs initial setup. The imaging device 20 sets a parameter "i" indicating a light source that will be turned on as, for example, "i=1," and the process proceeds to step ST2.

In step ST2, the imaging device 20 turns on an $i^{th}$ light source of the attachment device 71, and the process proceeds to step ST3.

In step ST3, the imaging device 20 performs focus adjustment. The imaging device 20 performs focus adjustment based on a captured image generated by an image sensor. Also, the imaging device 20 calculates an evaluation value indicating a focus state, and the process proceeds to step ST4. The evaluation value may be information that changes according to the focus state. For example, when focus adjustment is performed using a contrast method, the imaging device 20 calculates a difference in brightness level with an adjacent pixel for each pixel of a captured image as represented in equation (1), and uses the sum of absolute values of the differences in brightness level calculated for every pixels as an evaluation value Fv. In equation (1), "I(x,y)" represents a pixel value (brightness level) at a pixel position (x,y). Also, a plurality of evaluation regions may be set in the captured image, as represented in equation (2), the sum of absolute values of differences in brightness level with adjacent pixels may be calculated in each evaluation region, and the sums calculated for every regions may be summed up to be set as an evaluation value. In equation (2), "Bi" represents an ith region, and "I(x,y)" represents a pixel value (brightness level) at a pixel position (x,y) in the ith region Bi. For example, when focus adjustment is performed using a phase difference method, it is preferable for the imaging device 20 to use a phase difference of an optical image formed on a focus sensor of the phase difference method as an evaluation value. In addition, the imaging device 20 may extract high frequency components of a predetermined band from the captured image, and use the sum of absolute values of the extracted high frequency components as an evaluation value.

$$F_v = \sum_{x,y} (|I(x-1, y) - I(x, y)| + |I(x, y-1) - I(x, y)|) \quad (1)$$

$$F_v = \sum_{i} \sum_{x,y \in B_i} (|I(x-1, y) - I(x, y)| + |I(x, y-1) - I(x, y)|) \quad (2)$$

In step ST4, the imaging device 20 determines whether adjustment has been performed on all light sources. For example, when n light sources having different lighting directions are installed, the imaging device 20 determines that adjustment has been performed on all the light sources in the case of i=n, and the process proceeds to step ST6. In the case of i<n, the imaging device 20 determines that adjustment has not been performed on all the light sources, and the process proceeds to step ST5.

In step ST5, the imaging device 20 performs an arithmetic operation of "i=i+1" to update the parameter i, and the process returns to step ST2.

In step ST6, the imaging device 20 determines optimal focus. Based on the evaluation values calculated for every lighting directions, the imaging device 20 determines a lighting direction in which a focus state becomes best, and the process proceeds to step ST7.

In step ST7, the imaging device 20 carries out photography. The imaging device 20 provides lighting in the lighting direction determined in step ST6 and performs an imaging operation, thereby acquiring an image signal of a skin image.

By performing such a process, the imaging device 20 can readily obtain a good skin image. In addition, when the attachment device 71 automatically switches lighting directions, the imaging device 20 can determine a lighting direction in which a focus state becomes best by associating information indicating a lighting direction with an evaluation value.

Operation of FIG. 14 illustrates a case in which n light sources are caused to emit light in sequence, but if n light sources are caused to emit light in sequence, the time necessary for determining optimal focus lengthens when there are many light sources. Thus, the imaging device 20 thins out lighting directions in a circumferential direction, for example, thins out and turns on light sources disposed in a ring shape, and performs focus adjustment on a subject for each lighting direction after thinning out, thereby calculating an evaluation value in accordance with a focus state. Also, evaluation values of the thinned-out lighting directions, that is, light sources that have not emitted light, are calculated by interpolation. In this way, evaluation values for every lighting directions are calculated, so that a lighting direction in which a focus state becomes best can be determined from the calculated evaluation values in a short time.

Figure 15:
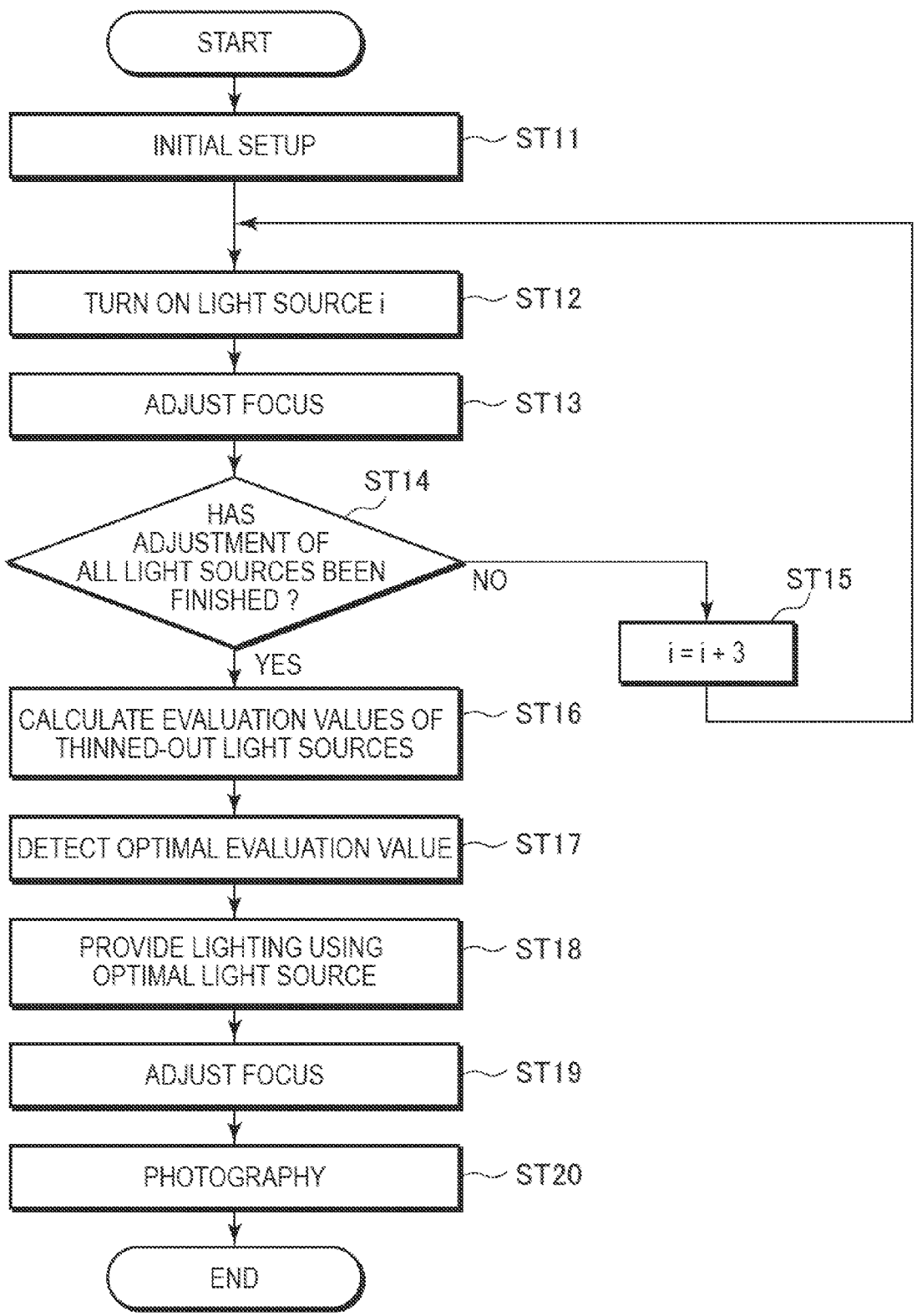
FIG. 15 is a flowchart illustrating operation of an imaging device when light sources are thinned out and caused to emit light.

FIG. 15 is a flowchart illustrating operation of an imaging device when light sources are thinned out and caused to emit light. FIG. 15 shows an example of a case in which the number of light sources is "24," and a thinning-out interval is "2." In step ST11, the imaging device 20 performs initial setup. The imaging device 20 sets a parameter "i" indicating a light source that will be turned on as, for example, "i=1," and the process proceeds to step ST12.

In step ST12, the imaging device 20 turns on an ith light source of the attachment device 71, and the process proceeds to step ST13.

In step ST13, the imaging device 20 performs focus adjustment. The imaging device 20 performs focus adjustment based on a captured image generated by an image sensor. Also, the imaging device 20 calculates an evaluation value indicating a focus state, and the process proceeds to step ST14.

In step ST14, the imaging device 20 determines whether adjustment has been performed on all light sources that emit light. When it is determined that adjustment has been performed on all the light sources emitting light, the process of the imaging device 20 proceeds to step ST16. When there remains a light source on which adjustment has not been finished among all the light sources emitting light, the process proceeds to step ST15.

In step ST15, the imaging device 20 performs an arithmetic operation of "i=i+3" to update the parameter i, and the process returns to step ST12.

In step ST16, the imaging device 20 calculates evaluation values of thinned-out light sources that have not emitted light. The imaging device 20 calculates the evaluation values of the thinning-target light sources that have not emitted light due to the thinning-out from evaluation values of light sources that have emitted light by interpolation, for example, spline interpolation or the like.

In step ST17, the imaging device 20 detects an optimal evaluation value. The imaging device 20 detects an evaluation value at which a focus state becomes best as the optimal evaluation value, and the process proceeds to step ST18.

In step ST18, the imaging device 20 provides lighting using an optimal light source. The imaging device 20 provides lighting using a light source corresponding to the optimal evaluation value, and the process proceeds to step ST19.

In step ST19, the imaging device 20 performs focus adjustment. The imaging device 20 performs focus adjustment in a state of lighting performed in step ST18, and the process proceeds to step ST20.

In step ST20, the imaging device 20 carries out photography. The imaging device 20 performs an imaging operation in the state of the lighting provided in step ST18 and a focus state adjusted in step ST19, thereby acquiring an image signal of a skin image.

Figure 16:
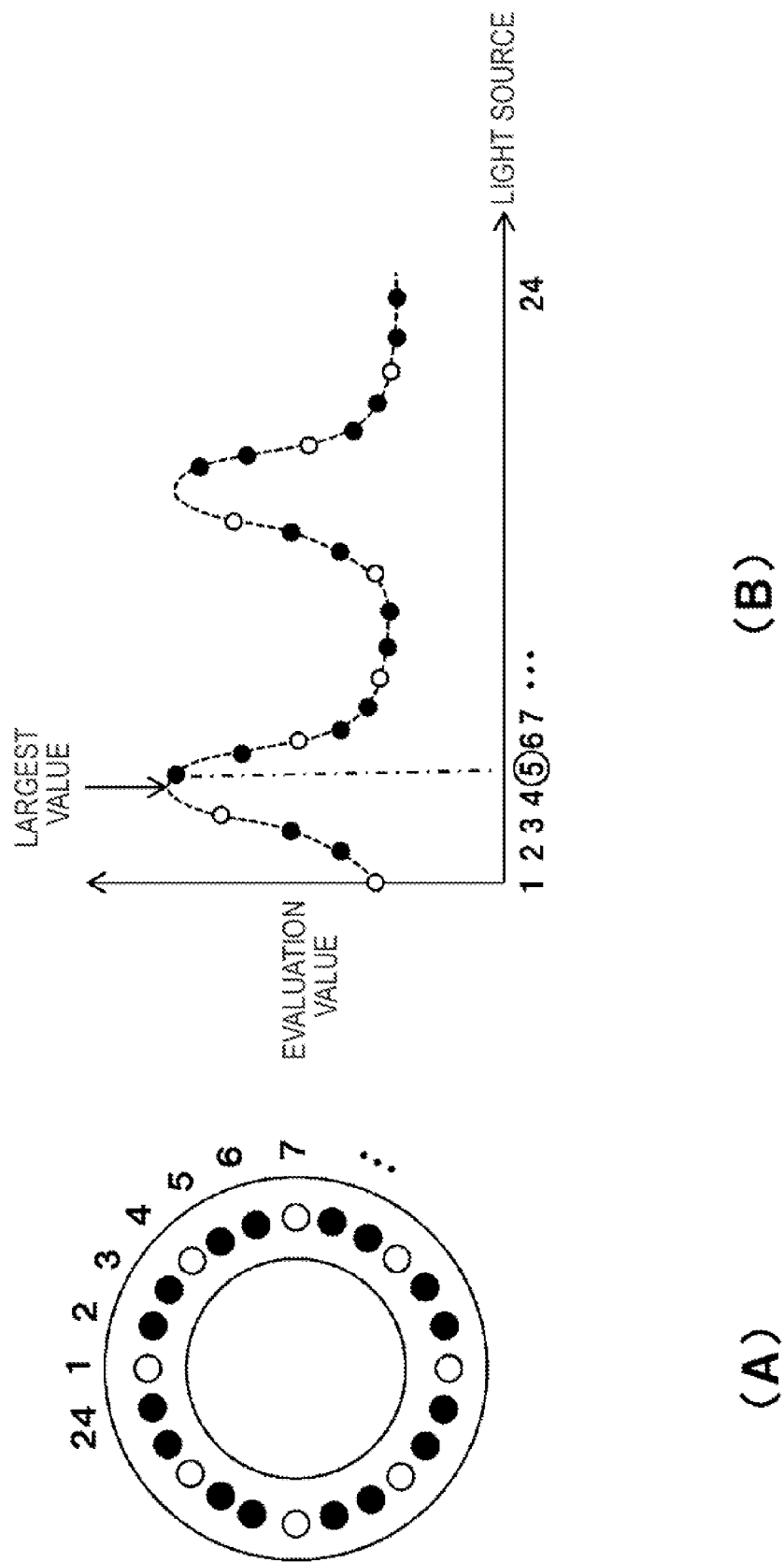
FIG. 16 is a diagram illustrating operation of an imaging device when light sources are thinned out and caused to emit light.

When such operation is performed, as shown in FIG. 16(A), light sources indicated by black circles are determined as thinning-target light sources, and light sources indicated by white circles are used in sequence to provide lighting, so that evaluation values (white circles) are calculated as shown in, for example, FIG. 16(B). In addition, evaluation values (black circles) of the other light sources are calculated by interpolation or the like. Furthermore, based on the evaluation values for every light sources, a light source by which a focus state becomes best, for example, a fifth light source whose evaluation value becomes the largest (light source indicated by a number in a circle), is used as a light source for lighting used in capturing to capture.

As a method of preventing lengthening of the time necessary until determining optimal focus, an adjustment range of a lighting direction may be reduced.

Figure 17:
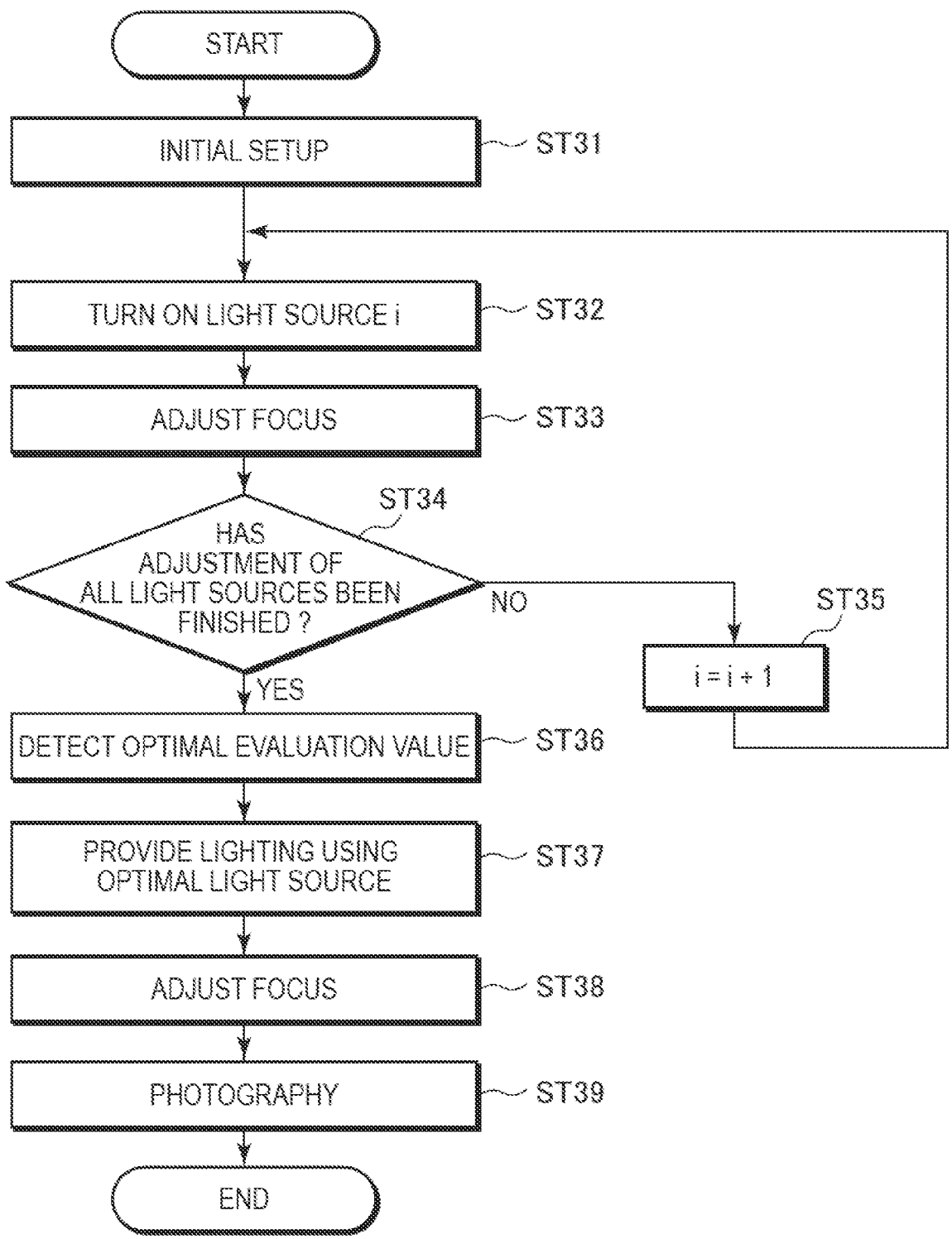
FIG. 17 is a flowchart illustrating operation of an imaging device when a lighting direction is set within an adjustment range of 0 to 180 degrees.

FIG. 17 is a flowchart illustrating operation of an imaging device when a lighting direction is set within an adjustment range of 0 to 180 degrees. For example, FIG. 17 shows a case in which the number of light sources is "24," and first to 12th light sources are selected in sequence and used for lighting. In step ST31, the imaging device 20 performs initial setup. The imaging device 20 sets a parameter "i" indicating a light source that will be turned on as, for example, "i=1," and the process proceeds to step ST32

In step ST32, the imaging device 20 turns on an ith light source of the attachment device 71, and the process proceeds to step ST33.

In step ST33, the imaging device 20 performs focus adjustment. The imaging device 20 performs focus adjustment based on a captured image generated by an image sensor. Also, the imaging device 20 calculates an evaluation value indicating a focus state, and the process proceeds to step ST34.

In step ST34, the imaging device 20 determines whether adjustment has been performed on all light sources that emit light. When it is determined that adjustment has been performed on all the light sources emitting light, that is, when i=12, the process of the imaging device 20 proceeds to step ST36. When adjustment on all the light sources emitting light has not been finished, the process proceeds to step ST35.

In step ST35, the imaging device 20 performs an arithmetic operation of "i=i+1" to update the parameter i, and the process returns to step ST32.

In step ST36, the imaging device 20 detects an optimal evaluation value. The imaging device 20 detects an evaluation value at which a focus state becomes best as the optimal evaluation value, and the process proceeds to step ST37.

In step ST37, the imaging device 20 provides lighting using an optimal light source. The imaging device 20 provides lighting using a light source corresponding to the optimal evaluation value, and the process proceeds to step ST38.

In step ST38, the imaging device 20 performs focus adjustment. The imaging device 20 performs focus adjustment in a state of the lighting provided in step ST37, and the process proceeds to step ST39.

In step ST39, the imaging device 20 captures. The imaging device 20 performs an imaging operation in the state of the lighting provided in step ST37 and a focus state adjusted in step ST38, thereby acquiring an image signal of a skin image.

Figure 18:
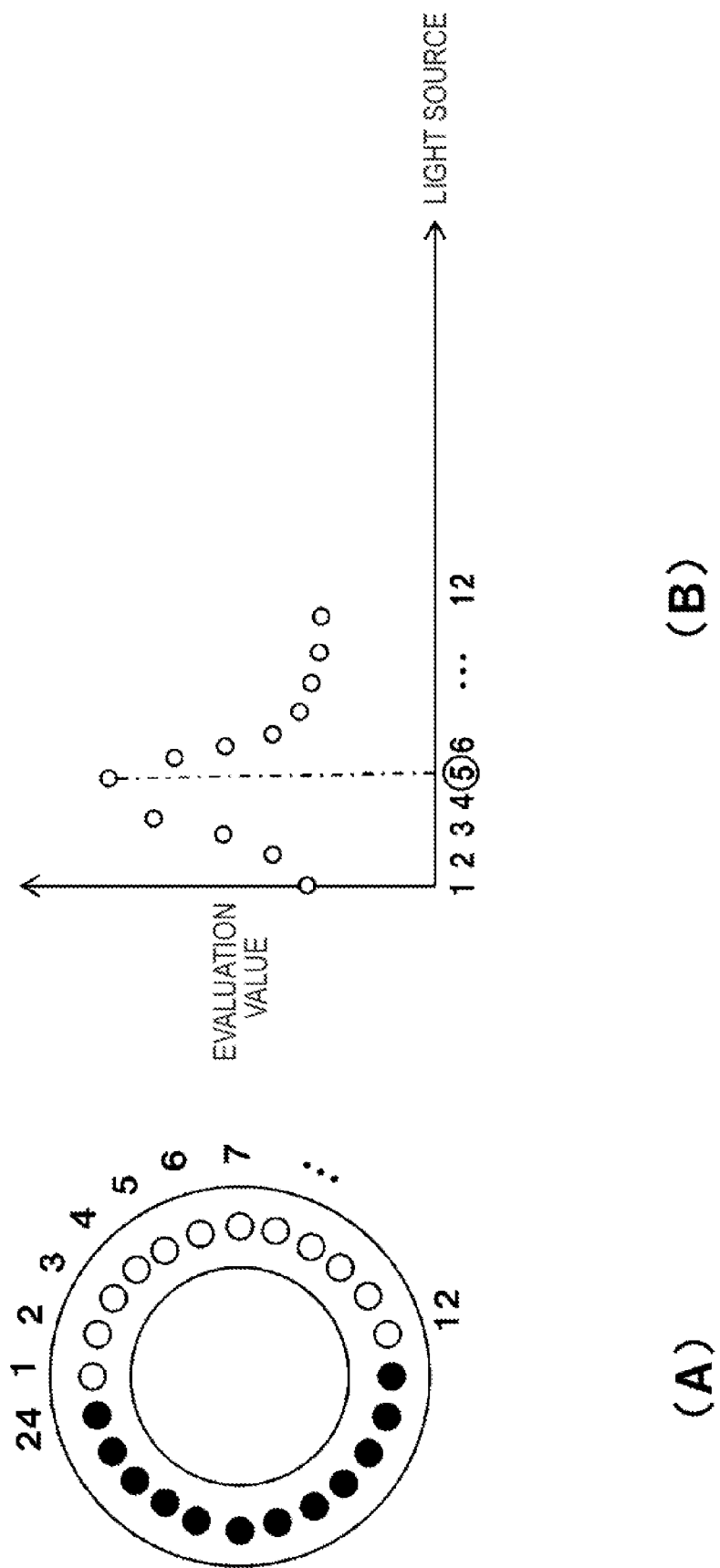
FIG. 18 is a diagram illustrating operation of an imaging device when a lighting direction is set within an adjustment range of 0 to 180 degrees.

When such operation is performed, as shown in FIG. 18(A), lighting is provided using only light sources indicated by white circles in sequence, and evaluation values are calculated as shown in, for example, FIG. 18(B). Based on the evaluation values for every light sources, a light source by which a focus state becomes best, for example, a fifth light source whose evaluation value becomes the largest (light source indicated by a number in a circle), is used as a light source for lighting used in capturing to capture.

Figure 19:
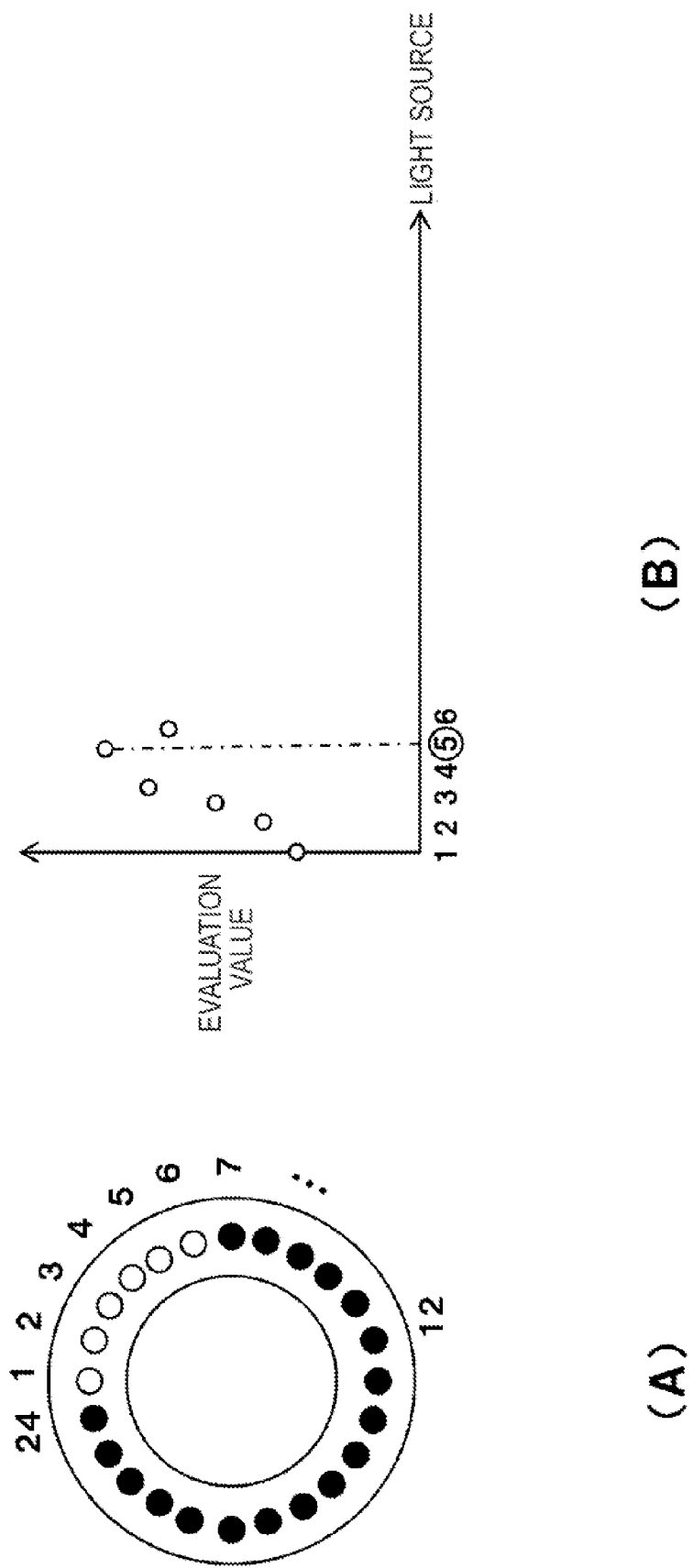
FIG. 19 is a diagram illustrating operation of an imaging device when an adjustment range of a lighting direction is further reduced.

In addition, when only the light sources indicated by the white circles are used in sequence to provide lighting as shown in FIG. 19, an adjustment range of a lighting direction can be further reduced to capture. In this case, in step ST34 of FIG. 17, the process may be performed to proceed to step ST36 when i=6.

Furthermore, even when n light sources are grouped, and light sources caused to emit light are switched in group units, it is possible to prevent lengthening of the time necessary until determining optimal focus.

Figure 20:
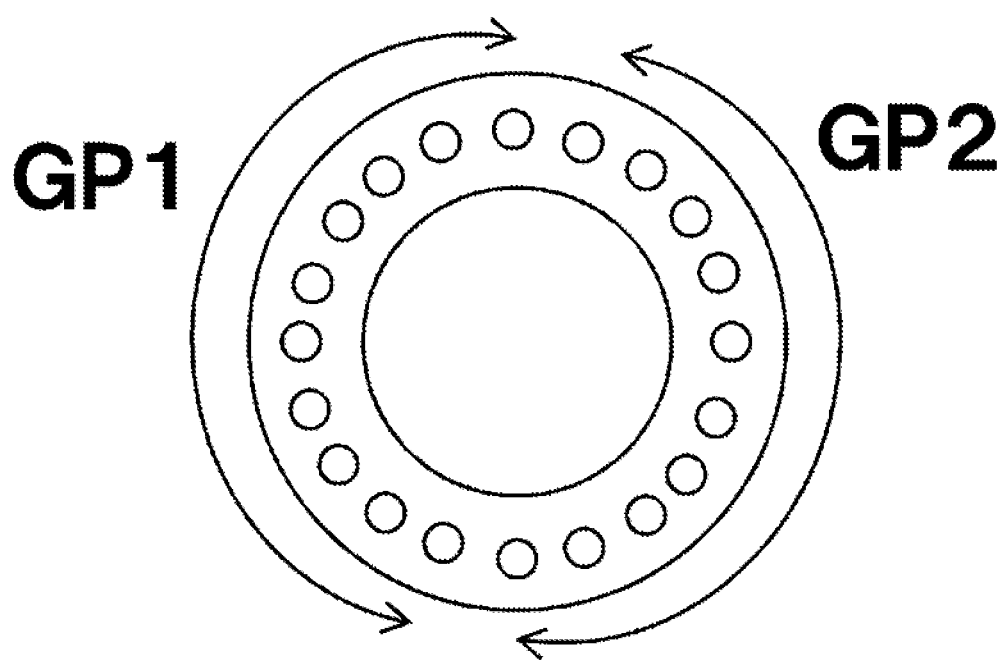
FIG. 20 is a diagram showing a case in which 20 light sources have been divided into two groups of ten consecutive light sources.
Figure 21:
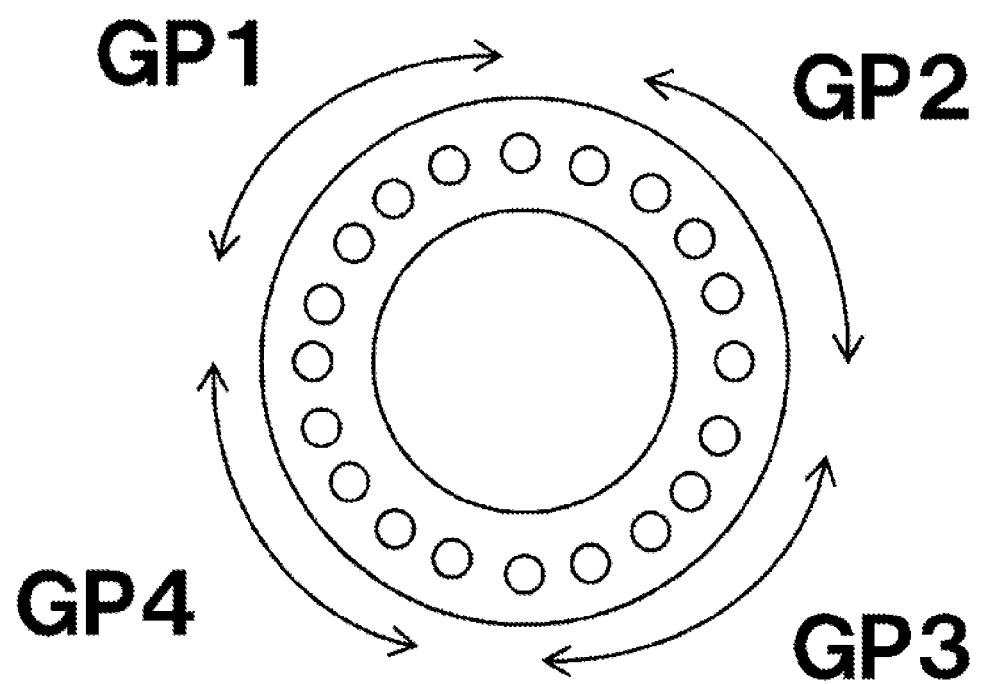
FIG. 21 is a diagram showing a case in which 20 light sources have been divided into four groups of five consecutive light sources.

FIG. 20 shows an example of a case in which 20 light sources have been divided into two groups of ten consecutive light sources, and FIG. 21 shows an example of a case in which 20 light sources have been divided into four groups of five consecutive light sources.

When n light sources are caused to emit light in sequence, the imaging device 20 is not limited to a case of sequentially causing the n light sources to emit light in group units, but may cause all the light sources to emit light, calculate evaluation values, and determine optimal focus in consideration of the calculated evaluation values as well.

Figure 22:
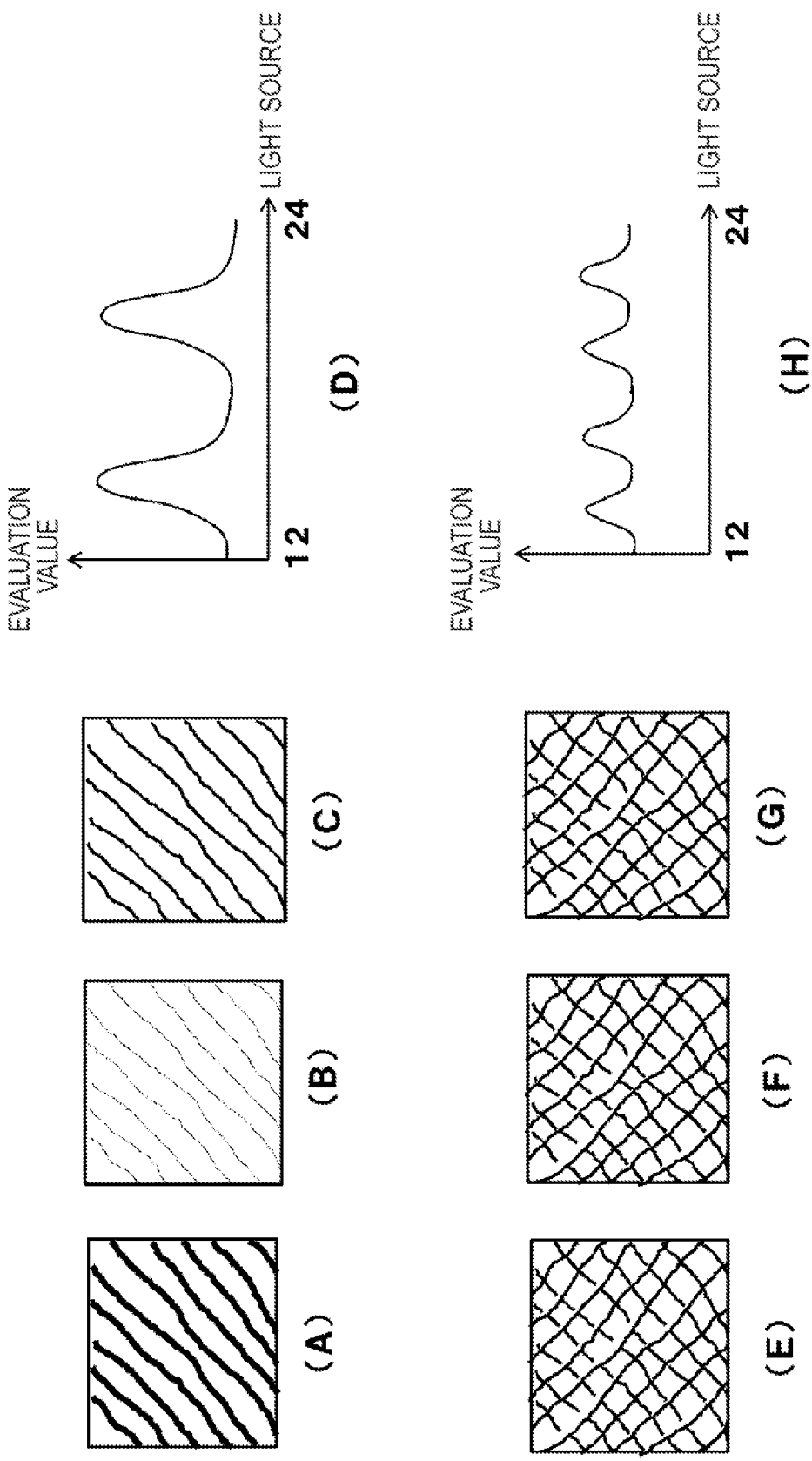
FIG. 22 is a diagram showing examples of images captured in the case of changing a lighting direction.

FIG. 22 shows examples of images captured in the case of changing a lighting direction. FIG. 22(A) shows an example of an image of a case in which lighting is provided in a perpendicular direction to a groove direction of wrinkles, FIG. 22(B) shows an example of the image of a case in which lighting is provided in a parallel direction to the groove direction of wrinkles, and FIG. 22(C) shows an example of an image of a case in which lighting is provided in all directions. Also, FIG. 22(D) shows examples of evaluation values of a case in which 24 light sources are switched and turned on in sequence. If wrinkles are noticed, an evaluation value becomes large when lighting is provided in a direction crossing the wrinkles at right angles, and thus there are two peaks when a lighting direction is moved by 360 degrees. Accordingly, when an evaluation value calculated from, for example, the image shown in FIG. 22(A) is determined as an evaluation value of a lighting direction in which a focus state becomes best, lighting is provided in the perpendicular direction to the groove direction of the wrinkles, and the focus adjustment is performed to capture. Also, FIGS. 22(E) to 22(G) show captured images of skin in which wrinkles are not noticed. FIG. 22(E) corresponds to the same lighting direction as that of FIG. 22(A), and FIGS. 22(F) and 22(G) correspond to the same lighting direction as that of FIGS. 22(B) and 22(C). If a shape of a skin bump of skin in which wrinkles are not noticed is, for example, a quadrilateral shape, there are four peaks as shown in FIG. 22(H) when a lighting direction is moved by 360 degrees.

When lighting is provided in a perpendicular direction to a groove direction of wrinkles, for example, an evaluation value becomes large, and when lighting is provided in a parallel direction to the groove direction of the wrinkles, an evaluation value becomes small. Thus, when perpendicular lighting directions are included in one group in the grouping described above, it becomes possible to determine a lighting direction in which a focus state becomes good in one group.

2-1-3. Another Configuration of Attachment Device

Figure 23:
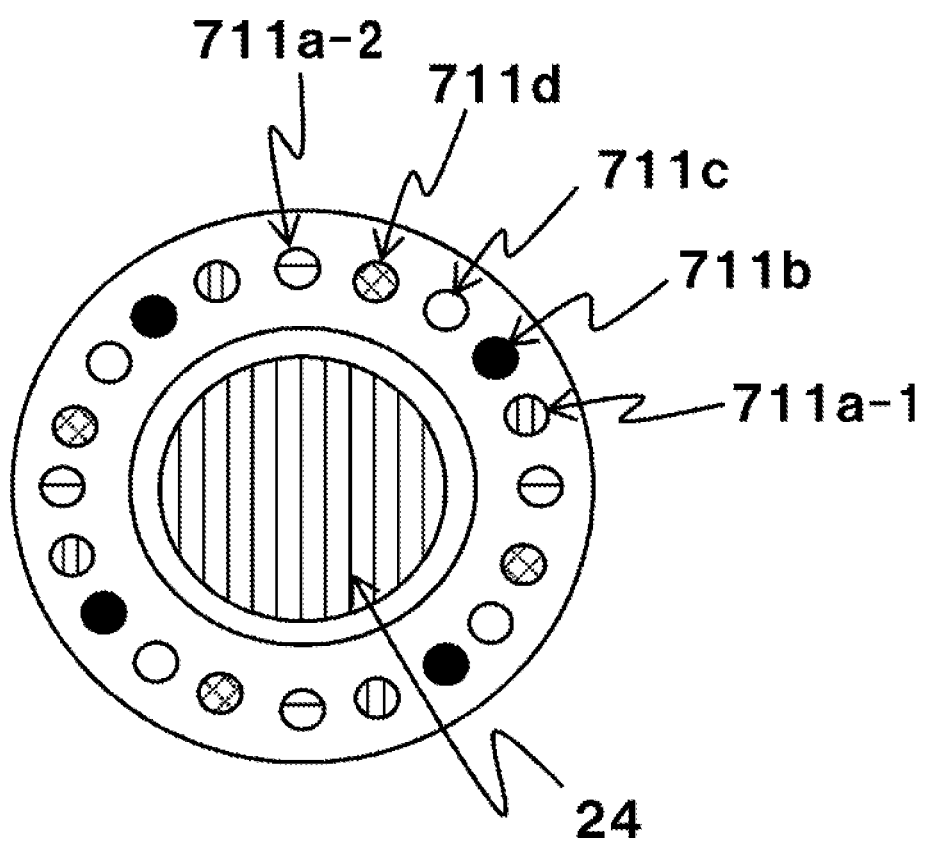
FIG. 23 is a diagram showing an example of a light source installed in an attachment device.
Figure 24:
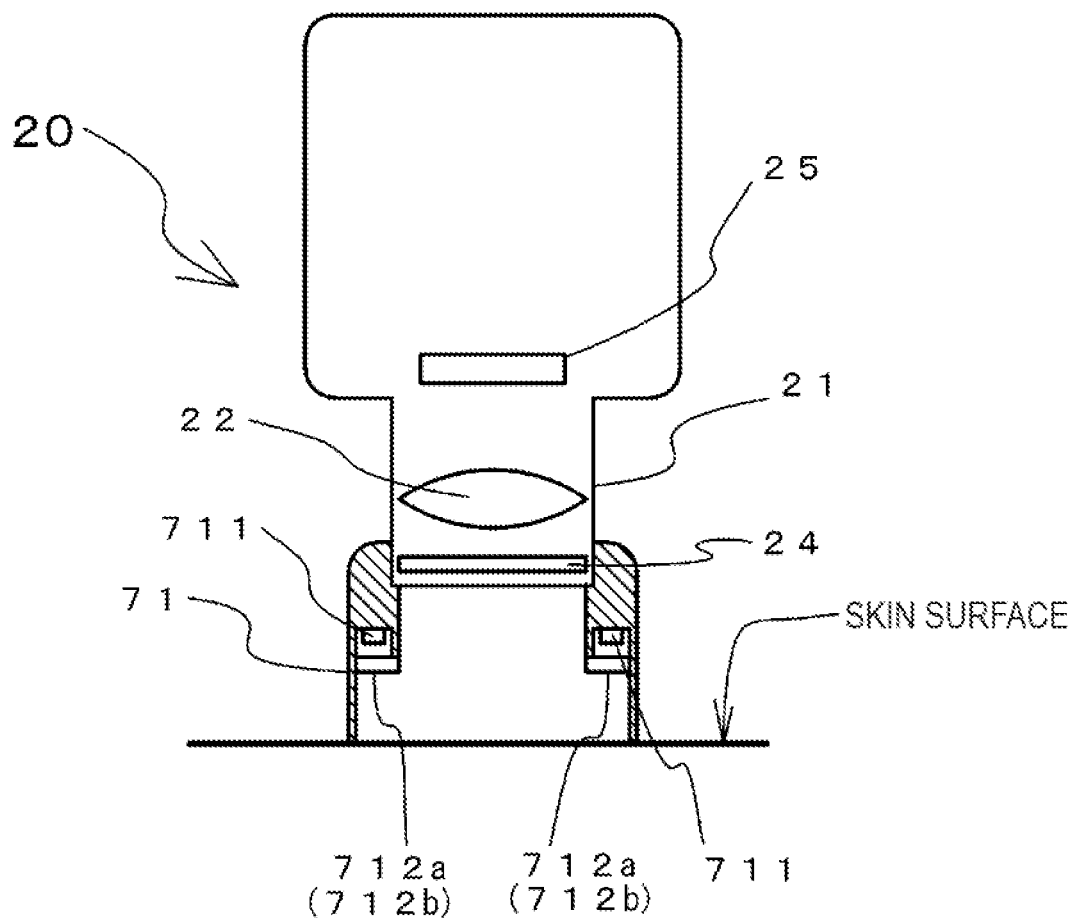
FIG. 24 is a diagram schematically showing an internal configuration of an imaging device.

Next, another configuration of an attachment device will be described. In the other configuration, a light source having an emission wavelength suitable for analysis is used as a light source or an external light source of the attachment device 71. For example, when an outer appearance such as texture, wrinkles, or the like of skin, is analyzed, a visible white LED (Light Emitting Diode) is used as a light source. When the state of melanin is analyzed, a visible red LED and a near infrared LED are used. When sebum filling pores is measured, a near ultraviolet LED is used. In addition, in order to separately capture surficial reflection light and internal reflection light, a polarizing filter may be installed in a light source. FIG. 23 and FIG. 24 correspond to FIG. 4 and FIG. 5 respectively, and show an example of a case in which white LEDs 711a, a visible red LED 711b, a near infrared LED 711c, and a near ultraviolet LED 711d are used as the plurality of light sources 711. Also, an example of a case is shown in which a white LED 711a-1 in which a polarizing filter of a predetermined polarizing plane is installed and a white LED 711a-2 in which a polarizing filter having, for example, a polarizing plane perpendicular to a predetermined polarizing plane is installed are installed. When a light source in which a polarizing filter is installed is used, a polarizing filter 24 is installed on an optical path to the image sensor 25 in the imaging device 20, and subject light in a desired polarization state is incident on the image sensor 25 through the imaging optical system 22.

Figure 25:
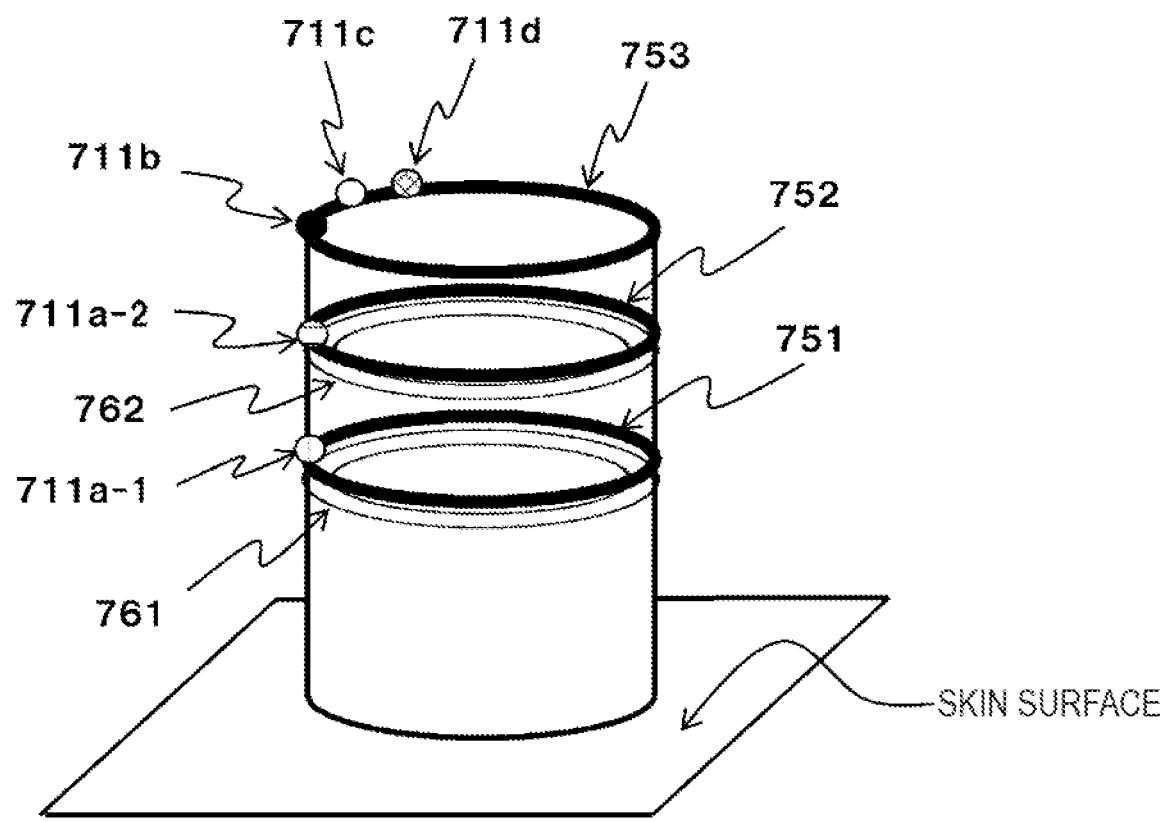
FIG. 25 is a diagram showing an example of a case in which a light source and a light guide path are combined.
Figure 26:
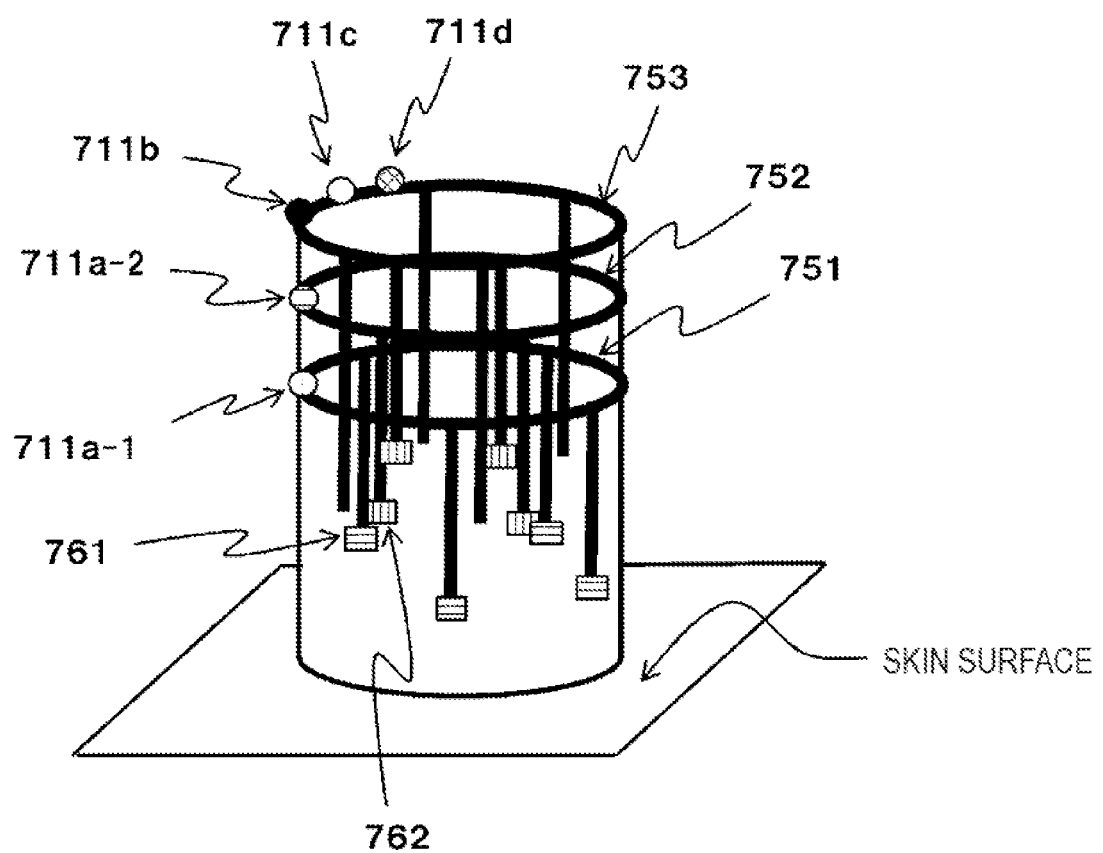
FIG. 26 is a diagram showing an example of a case in which a light source and a light guide path are combined.

The attachment device 71 may be configured by combining light sources and light guide paths. FIGS. 25 and 26 show examples of a case in which light sources and light guide paths are combined. For example, illumination light output from a white LED 711a-1 is irradiated on a subject (skin surface) through a light guide path 751. On an inclined illumination light output surface of the light guide path 751, a polarizing filter 761 is installed. Also, illumination light output from a white LED 711a-2 is irradiated on the subject (skin surface) through a light guide path 752. On an inclined illumination light output surface of the light guide path 752, a polarizing filter 762 is installed. Polarizing planes of the polarizing filter 761 and the polarizing filter 762 are made to cross at right angles. Furthermore, illumination light emitted from the visible red LED 711b, the near infrared LED 711c, and the near ultraviolet LED 711d is irradiated on the subject (skin surface) through a light guide path 753. Although not shown in the drawings, when no polarizing filter is used, the illumination light output from the white LEDs 711a may be irradiated on the subject (skin surface) through the light guide path 753.

As described above, when light sources having different emission wavelengths or polarizing filters are used, the imaging device 20 selects light sources suitable for analysis, turns on the selected light sources in sequence, determines a lighting direction in which a focus state becomes best as described above, and captures in a determined lighting state. In this way, the imaging device 20 can generate an optimal captured image according to analysis content. When focus states are different due to emission wavelengths of light sources, focus adjustment may be performed using the amount of adjustment calculated in advance according to the emission wavelengths of the light sources. Also, focus adjustment may be performed using the light sources used in analysis.

2-1-4. Focus Operation of Imaging Device

Figure 27:
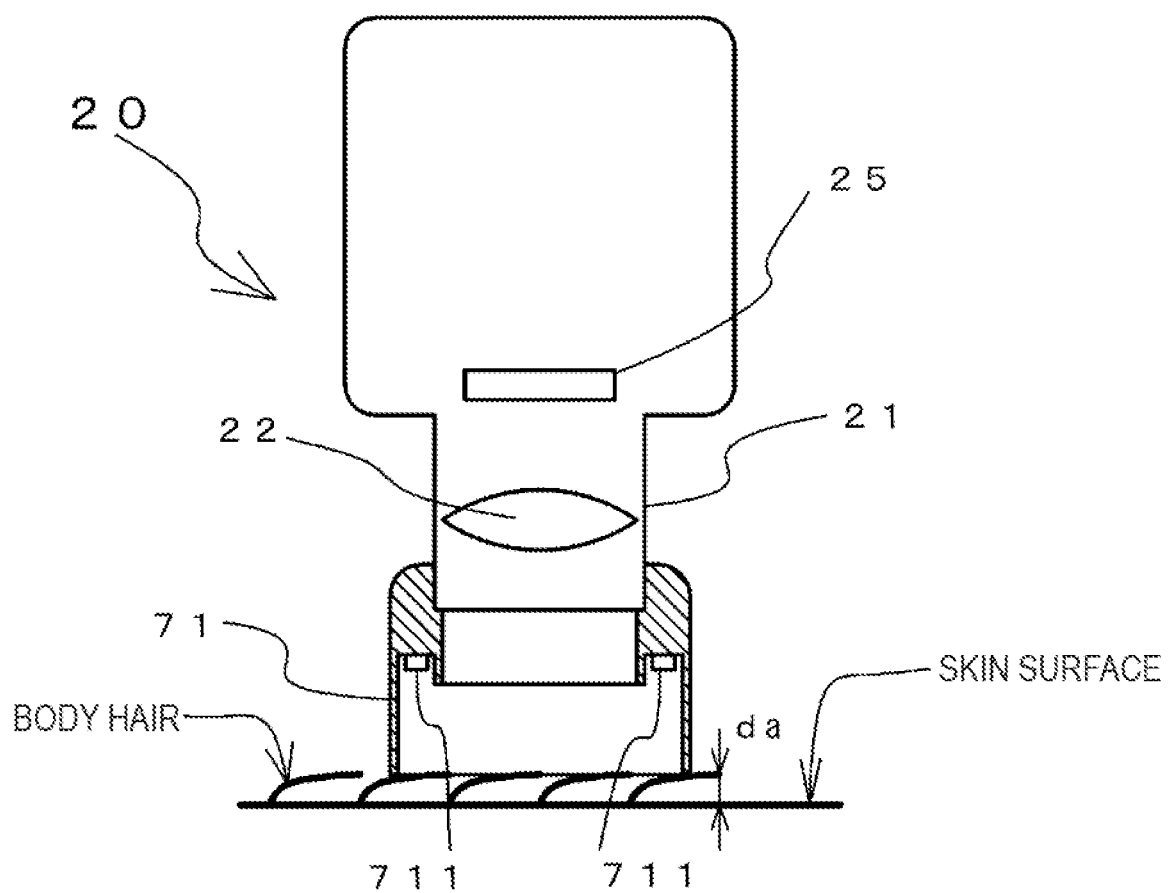

The imaging device 20 has an autofocus function such as the contrast method, the phase difference method, or the like. When such an autofocus function is used, it is assumed that there are a plurality of distances at which evaluation values become high. For example, if there are body hairs and the like as shown in FIG. 27 when a skin surface is captured, an evaluation value becomes high due to distance up to the body hairs as well as distance up to the skin surface. In such a case, it is assumed a case that the body hairs are in focus, but the skin surface is out of focus.

Figure 28:
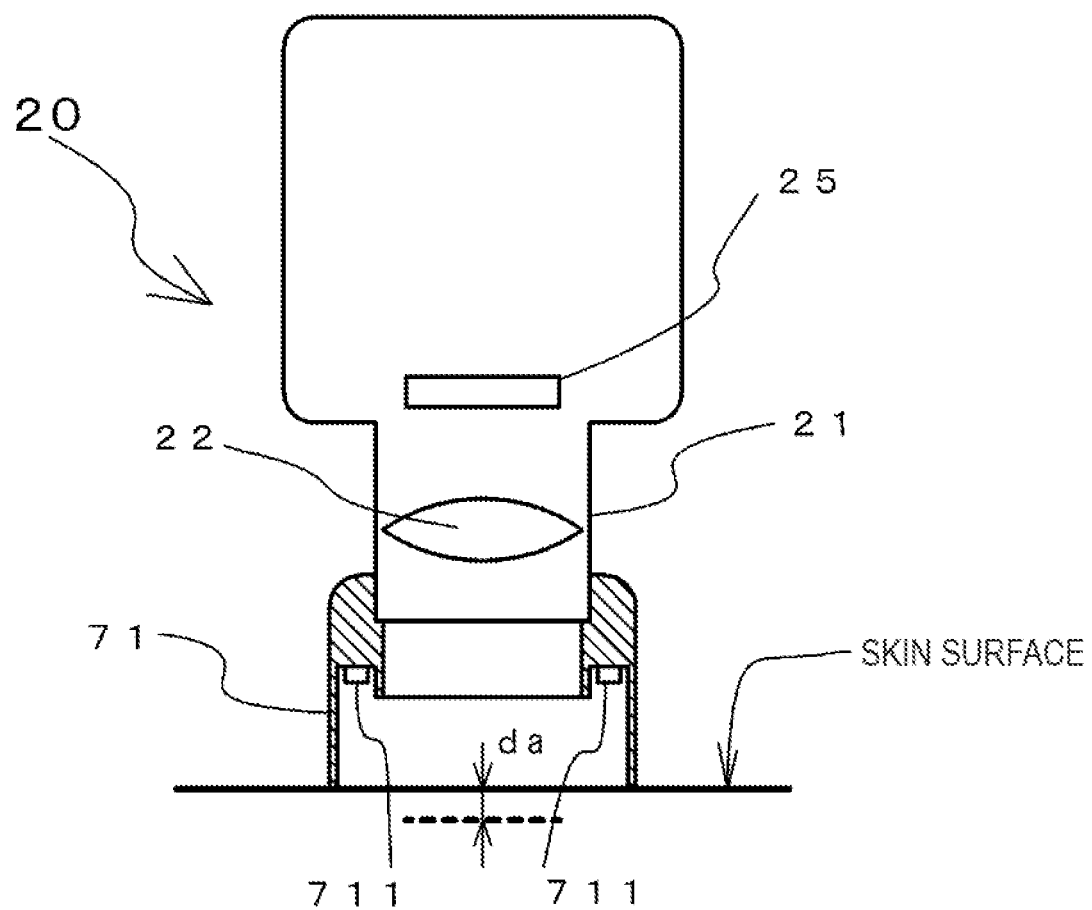
FIG. 28 is a diagram showing a case in which information is acquired by focusing on the inside of skin.

Accordingly, the imaging device 20 moves a focus position by a predetermined distance with respect to a focus adjustment position at which a focus state becomes best based on the evaluation values. For example, when there are a plurality of distances at which evaluation values become high, assuming that the shortest distance of the plurality of distances as a body hair part, focus adjustment may be performed to bring a position apart from the shortest distance by a distance da (the space between the body hairs and the skin surface) into focus, so that the surface of the subject comes into focus. Also, the imaging device 20 may use a lens that has the depth of field focused within a range of the distance da so that both of the body hairs and the skin surface are included in a focusing range. Furthermore, by moving the focus position by the distance da, it is possible to focus on the inside of skin as shown in FIG. 28 as well as the skin surface and acquire information.

2-2. Regarding Analysis Device

Figure 29:
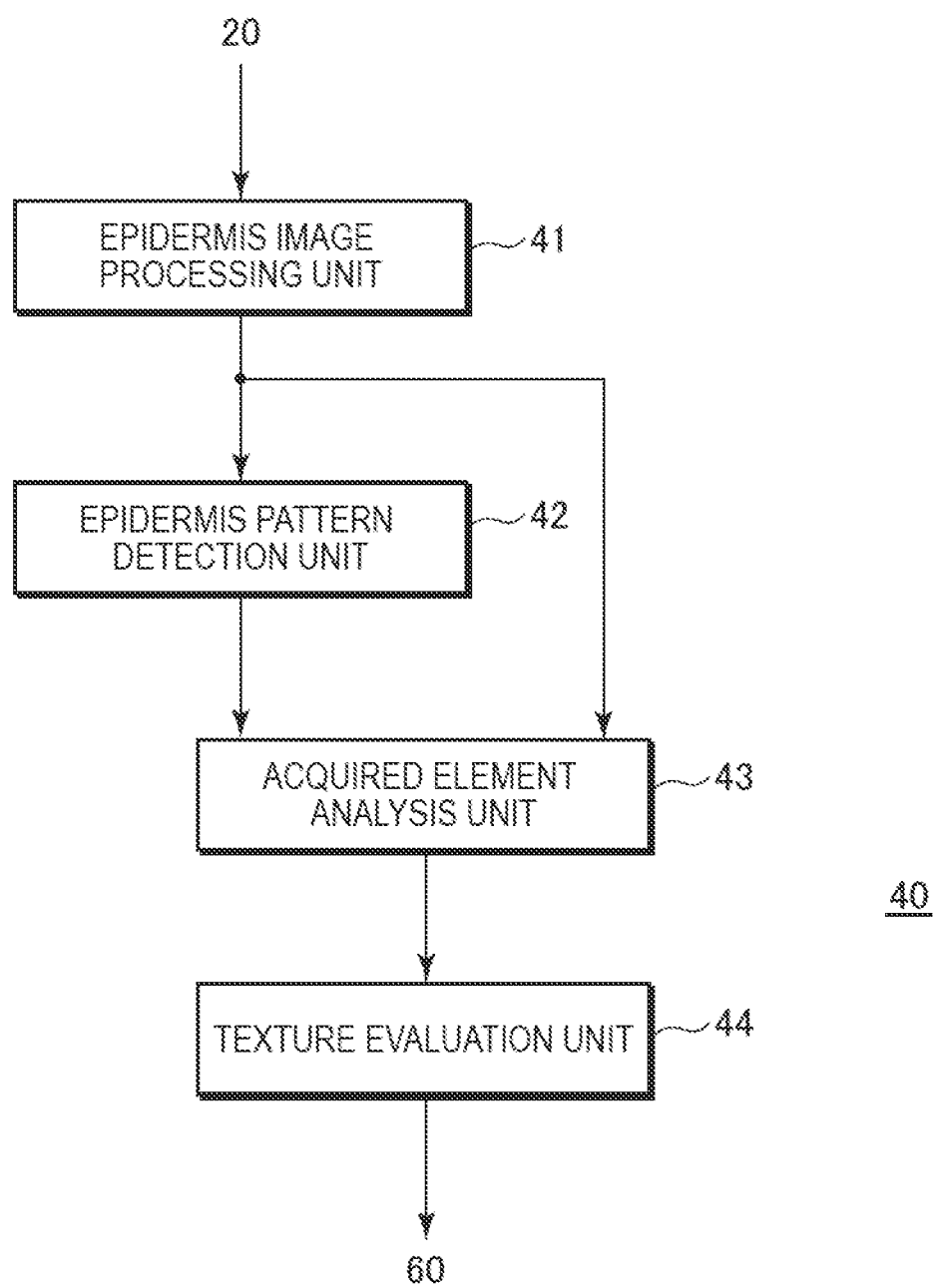
FIG. 29 is a diagram showing an example of a configuration of an analysis device.

FIG. 29 shows an example of a configuration of an analysis device. The analysis device 40 captures an analysis target, for example, the skin of an evaluatee, and evaluates a texture state or the like of the skin based on an image (hereinafter referred to as epidermis image) obtained as the results. Also, the analysis device 40 segments the epidermis image (region segmentation), and evaluates the texture state of the skin based on the results.

The analysis device 40 is configured to include an epidermis image processing unit 41, an epidermis pattern detection unit 42, an acquired element analysis unit 43, and a texture evaluation unit 44.

The epidermis image processing unit 41 performs a predetermined image process such as correction, noise removal, or the like on the epidermis image, and supplies the epidermis image after the image process to the epidermis pattern detection unit 42 and the acquired element analysis unit 43.

The epidermis pattern detection unit 42 detects a pattern of an epidermis (hereinafter referred to as an epidermis pattern) in the epidermis image formed on the epidermis by skin bumps or skin grooves, and supplies the detection results (hereinafter referred to as the epidermis pattern detection results) to the acquired element analysis unit 43.

The acquired element analysis unit 43 analyzes an acquired element among elements indicating the texture state of the skin based on the epidermis image after the image process and the epidermis pattern detection results. The acquired element analysis unit 43 supplies the analysis results to the texture evaluation unit 44.

The texture evaluation unit 44 evaluates the texture state of the skin based on the analysis results of the acquired element analysis unit 43, and outputs the evaluation results to the display device 60.

Figure 30:
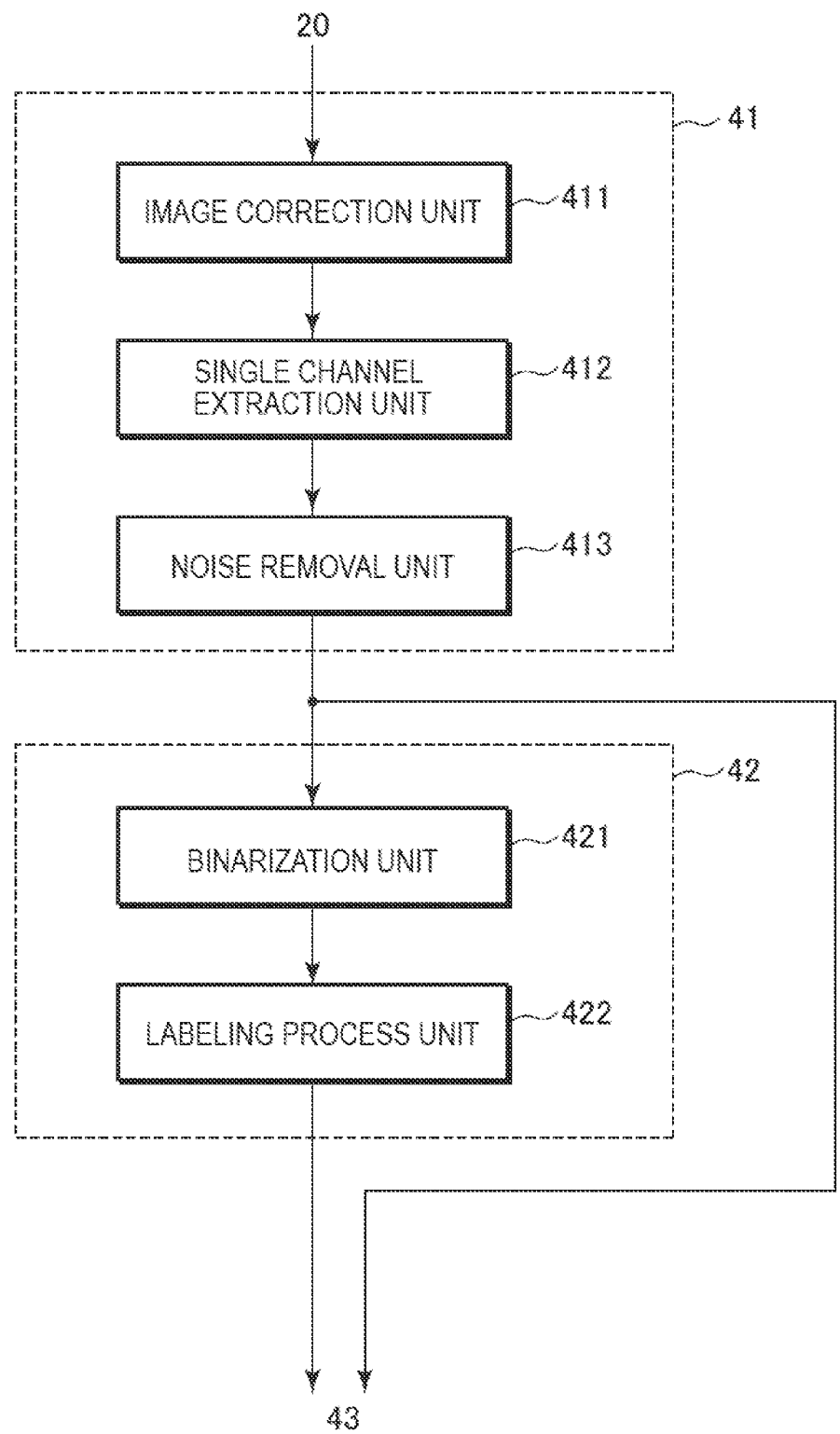
FIG. 30 is a block diagram showing examples of functional configurations of an epidermis image processing unit and an epidermis pattern detection unit.

FIG. 30 is a block diagram showing examples of functional configurations of the epidermis image processing unit 41 and the epidermis pattern detection unit 42.

The epidermis image processing unit 41 is configured to include an image correction unit 411, a single channel extraction unit 412, and a noise removal unit 413. The epidermis pattern detection unit 42 is configured to include a binarization unit 421 and a labeling process unit 422.

The image correction unit 411 performs shading correction, correction of lens distortion, excision of the central region of the epidermis image, and the like on the epidermis image. Also, the image correction unit 411 downsizes the image after correction so as to cut down processing cost. The image correction unit 411 supplies the epidermis image after correction to the single channel extraction unit 412.

The single channel extraction unit 412 extracts signal components of a predetermined channel, for example, a B (Blue) channel, from the corrected epidermis image, and supplies an epidermis image (hereinafter referred to as a single channel epidermis image) including the extracted signal components to the noise removal unit 413.

The noise removal unit 413 removes noise of the single channel epidermis image. The noise removal unit 413 applies an edge-preserving smoothing filter to the single channel epidermis image so as to remove random noise or texture components of skin bumps and skin grooves. Also, the noise removal unit 413 applies an isolated point removing filter to the single channel epidermis image so as to remove a high-brightness region or mirror surface reflection components influenced by, for example, sweat glands. The noise removal unit 413 supplies the single channel epidermis image after noise removal (hereinafter referred to as a noise-removed epidermis image) to the binarization unit 421 and the labeling process unit 422 of the epidermis pattern detection unit 42.

The binarization unit 421 performs a binarization process on the noise-removed epidermis image. Assuming that, under the uniform light source, a bright region of the epidermis image is a skin bump present on the front, and a dark region is a skin groove present in the inside, the binarization unit 421 binarizes the noise-removed epidermis image so as to segment skin bumps and skin grooves. The binarization unit 421 supplies the obtained binarization image (hereinafter referred to as a binarized epidermis image) to the labeling process unit 422.

The labeling process unit 422 performs labeling on the binarized epidermis image. The labeling process unit 422 detects a region surrounded by the outermost white outline as one region, and ignores black regions or regions surrounded by white outlines in the detected region. In this way, a label is given to the detected region. For this reason, for example, regions that become dark due to depressions inside skin bumps and the like are ignored, so that the skin bumps can be accurately detected. The region to which the label is given by a labeling process will be referred to as a labeling region below.

Considering that, in the skin of common people, a space between skin grooves is 0.25 to 0.5 mm, and many skin bumps have a triangular or quadrilateral shape, an area of a skin bump may be about 0.031 to 0.25 square millimeters. Thus, the labeling process unit 422 calculates an appropriate range of the size of a skin bump in the epidermis image. Among detected labeling regions, the labeling process unit 422 detects regions having sizes within the obtained appropriate range as skin bump regions.

The labeling process unit 422 counts the number of detected skin bump regions as a skin bump number. The labeling process unit 422 supplies the epidermis pattern detection results indicating the detection results of the skin bump regions and the skin bump number to the acquired element analysis unit 43.

Figure 31:
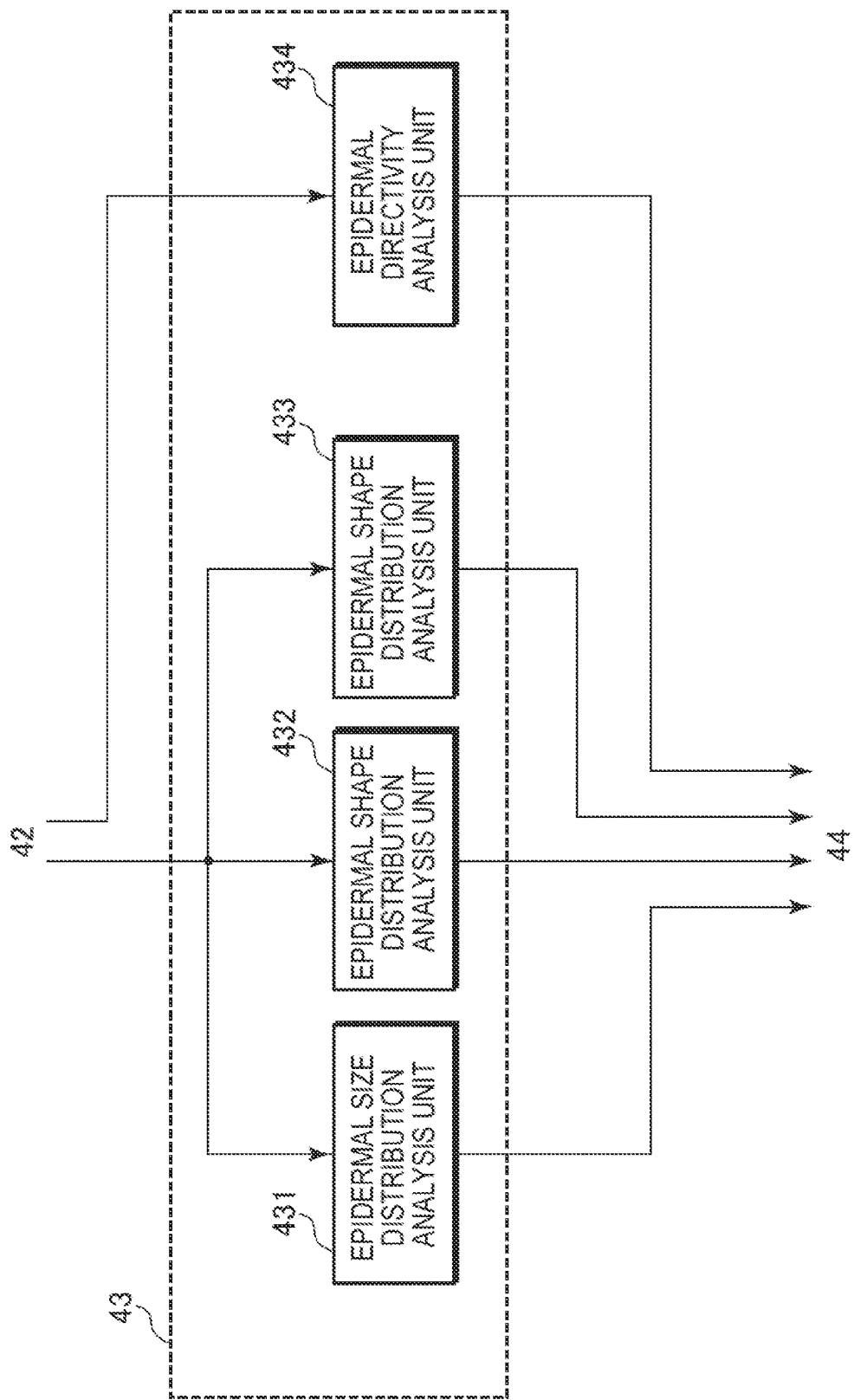
FIG. 31 is a block diagram showing an example of a functional configuration of an acquired element analysis unit.

FIG. 31 is a block diagram showing an example of a functional configuration of the acquired element analysis unit 43. The acquired element analysis unit 43 is configured to include an epidermal size distribution analysis unit 431, epidermal shape distribution analysis units 432 and 433, and an epidermal directivity analysis unit 434.

The epidermal size distribution analysis unit 431 analyzes the distribution of sizes of epidermis patterns. The epidermal size distribution analysis unit 431 analyzes the distribution of sizes of skin bump regions, and calculates an epidermal size distribution evaluation value representing the uniformity of the sizes of the skin bump regions. The epidermal size distribution analysis unit 431 supplies the calculated epidermal size distribution evaluation value to the texture evaluation unit 44.

The epidermal shape distribution analysis unit 432 analyzes the distribution of shapes of epidermis patterns. The epidermal shape distribution analysis unit 432 analyzes the distribution of shapes of the skin bump regions, and calculates an epidermal shape distribution evaluation value representing the uniformity of the shapes of the skin bump regions. The epidermal shape distribution analysis unit 432 supplies the calculated epidermal shape distribution evaluation value to the texture evaluation unit 44.

The epidermal shape distribution analysis unit 433 analyzes the distribution of shapes of the epidermis patterns from a point of view different from that of the epidermal shape distribution analysis unit 432. The epidermal shape distribution analysis unit 433 compares each of the skin bump regions with predetermined reference shapes, and obtains epidermal shape distribution information indicating a ratio of skin bump regions having shapes close to the respective reference shapes. The epidermal shape distribution analysis unit 433 supplies the obtained epidermal shape distribution information to the texture evaluation unit 44.

The epidermal directivity analysis unit 434 analyzes the directivity of the epidermis patterns. The epidermal directivity analysis unit 434 analyzes the distribution of edge directions of the skin bump regions, and calculates an epidermal directivity evaluation value representing the uniformity of the distribution of edge directions of the skin bump regions. The epidermal directivity analysis unit 434 supplies the calculated epidermal directivity evaluation value to the texture evaluation unit 44.

In addition, the sizes, the shapes, and the edge directions of the skin bumps change in an acquired manner depending on aging, health, skin care, and the like. Accordingly, the epidermal size distribution evaluation value, the epidermal shape distribution evaluation value, the epidermal shape distribution information, and the epidermal directivity evaluation value become indexes for evaluating acquired properties of the texture state of the skin.

The texture evaluation unit 44 calculates a texture evaluation value. From the epidermal size distribution evaluation value, the epidermal shape distribution evaluation value, and the epidermal directivity evaluation value, the texture evaluation unit 44 calculates a texture evaluation value that changes according to the uniformity of sizes of the skin bumps, the uniformity of shapes of the skin bumps, and the uniformity of the distribution of directions of the skin bumps. The uniformity of sizes of the skin bumps, the uniformity of shapes of the skin bumps, and the uniformity of the distribution of directions of the skin bumps change in an acquired manner depending on aging, health, care, and the like. Accordingly, the texture evaluation value becomes an index for evaluating the uniformity of the skin texture that changes in an acquired manner. In addition to the uniformity of texture, a texture evaluation value may be calculated to indicate a ratio of skin bumps having an ideal shape. The texture evaluation unit 44 outputs the evaluation results of the state of the skin texture to the display device 60.

2-3. Regarding Display Device

The display device 60 displays the evaluation results of the texture state of the skin on the screen. For example, as shown in FIG. 2, the display device 60 separately shows the fineness of texture, the condition of texture (the uniformity of sizes of the skin bumps, the uniformity of shapes of the skin bumps, the uniformity of the distribution of directions of the skin bumps, and the like), freckles, wrinkles, and the like in a radar chart.

In this way, the evaluatee becomes able to instantly know his or her own skin condition. Also, by displaying a skin image based on which a texture state is evaluated, or skin images that have been photographed before and after emission wavelengths of a light source are switched, it becomes possible to check not only the evaluation results but also a skin condition, a freckle condition, or the like.

As described above, in the first embodiment, a state in which, for example, the contrast of a captured image becomes highest is created by switching lighting directions, and focus is set in the state, so that a focus state can be adjusted to an optimal focus state. In other words, it becomes possible to set the focus based on wrinkles and the like of a skin surface. Accordingly, even without preparing a specific pattern and the like that become references, focus adjustment can be accurately performed.

3. Second Embodiment

When an image having low contrast is taken as in a case of taking a close-up image of skin, it is difficult to set the focus, and thus JP 2005-070300A discloses installing a pattern for autofocus on a fulcrum and performing focus control based on the pattern. However, in this technology, it is neither possible to acquire accurate color data nor to measure a reflectance. Also, JP 2002-345760A discloses making correction with a cap for correcting spectral reflectance put on and performing measurement without the cap. In this technology, an annoying operation that is putting on and taking off of the cap is necessary, and it is not possible to readily make correction.

Thus, in the following second embodiment, description will be made regarding a case of installing a reference pattern in an attachment device, enabling the focus to be set even in a low contrast state as in a close-up image of skin, and acquiring a good skin image. Also, using a region that becomes a reference of reflectance, automatic reflectance correction is allowed to be performed.

In the second embodiment, the imaging device 20 controls a zoom lens so that a focus adjustment pattern to be described later comes in the field of vision, and a sufficient region to perform focus control is shown, and then controls the focus so that the focus adjustment pattern comes into focus. Also, when no spectral reflectance correction pattern is shown in the field of vision, the imaging device 20 controls the zoom lens in a focus state as is so that a spectral reflectance correction pattern comes in the field of vision, and turns on respective light sources to photograph the pattern for correction and make correction of reflectance. Furthermore, the imaging device 20 controls the zoom lens in a focus state as is so that a subject region comes in the whole field of vision, and then turns on light sources having respective emission wavelengths to photograph the subject region and acquire image signals of a captured image at the respective wavelengths. Using the acquired image signals, the analysis device 40 performs analysis processes of the texture, color, and the like of skin. The display device 60 presents the analysis results.

3-1. Configuration of Imaging Device

Figure 32:
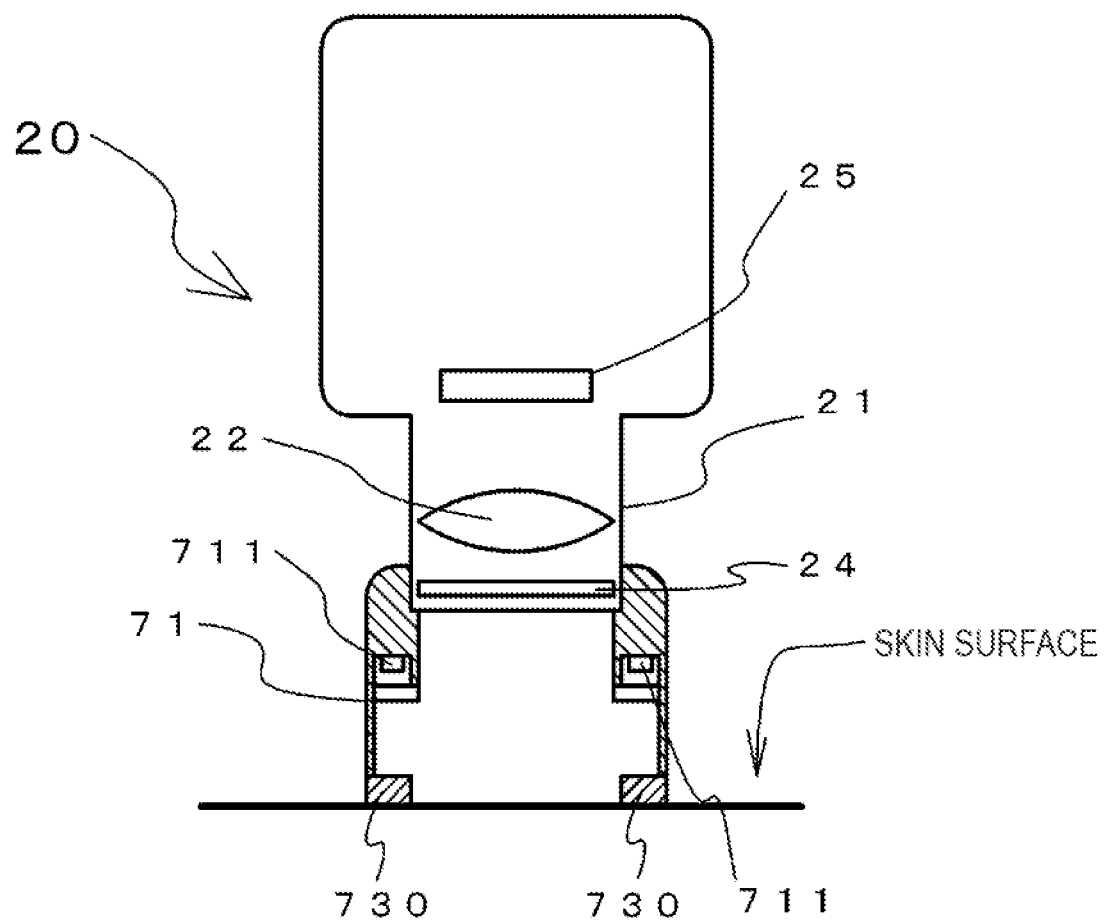
FIG. 32 is a diagram schematically showing an internal configuration of an imaging device.

In the imaging device 20 of the second embodiment, as shown in FIG. 32, a reference pattern unit 730 in a ring shape is disposed on the front end of the attachment device 71. On the inner side of the reference pattern unit 730, a reference pattern for performing focus adjustment, reflectance correction, or the like is installed.

Figure 33:
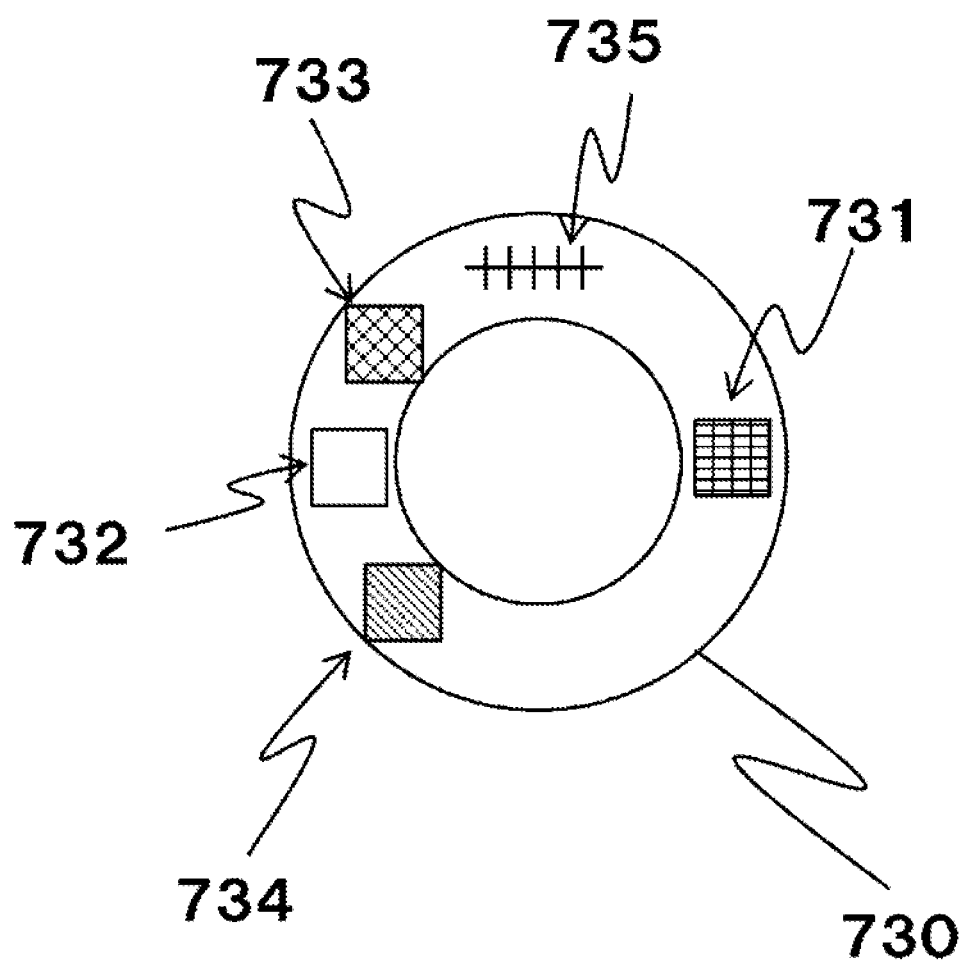
FIG. 33 is a diagram showing an example of a reference pattern.

FIG. 33 shows an example of a reference pattern. For example, a pattern for focus adjustment and a reflectance correction pattern are installed as reference patterns. In addition, a pattern for checking a subject size is installed so as to determine the size of a subject.

A focus adjustment pattern 731 is configured with an edge of high contrast and the like. The focus adjustment pattern 731 includes a low spatial frequency pattern so that the pattern can be found in an image even if the image is out of focus. In addition, the focus adjustment pattern 731 includes a high spatial frequency pattern so as to set the focus with high accuracy. Furthermore, the focus adjustment pattern 731 may use a pattern drawn with ink that can be photographed using all light sources in use, or patterns drawn with separate inks for every wavelength bands of light sources.

A pattern for reflectance correction is configured with a material that has a high reflectance in a wavelength band in which measurement is performed. Correction may be made using a material that has a high reflectance in an overall wavelength range in which measurement is performed, and a wavelength band may be configured to be divided into, for example, an ultraviolet light region, a visible light region, an infrared light region, and the like. For example, in FIG. 33, reflectance correction patterns 732, 733 and 734 are installed. The reflectance correction pattern 732 is a reference pattern for correcting a reflectance when visible light is used. The reflectance correction pattern 733 is a reference pattern for correcting a reflectance when near infrared light is used. The reflectance correction pattern 734 is a reference pattern for correcting a reflectance when ultraviolet light is used.

A pattern 735 for checking a subject size is configured as a scale pattern for checking a subject size. The pattern 735 is used as a reference for visually checking a subject size or measuring size by image processing.

Figure 34:
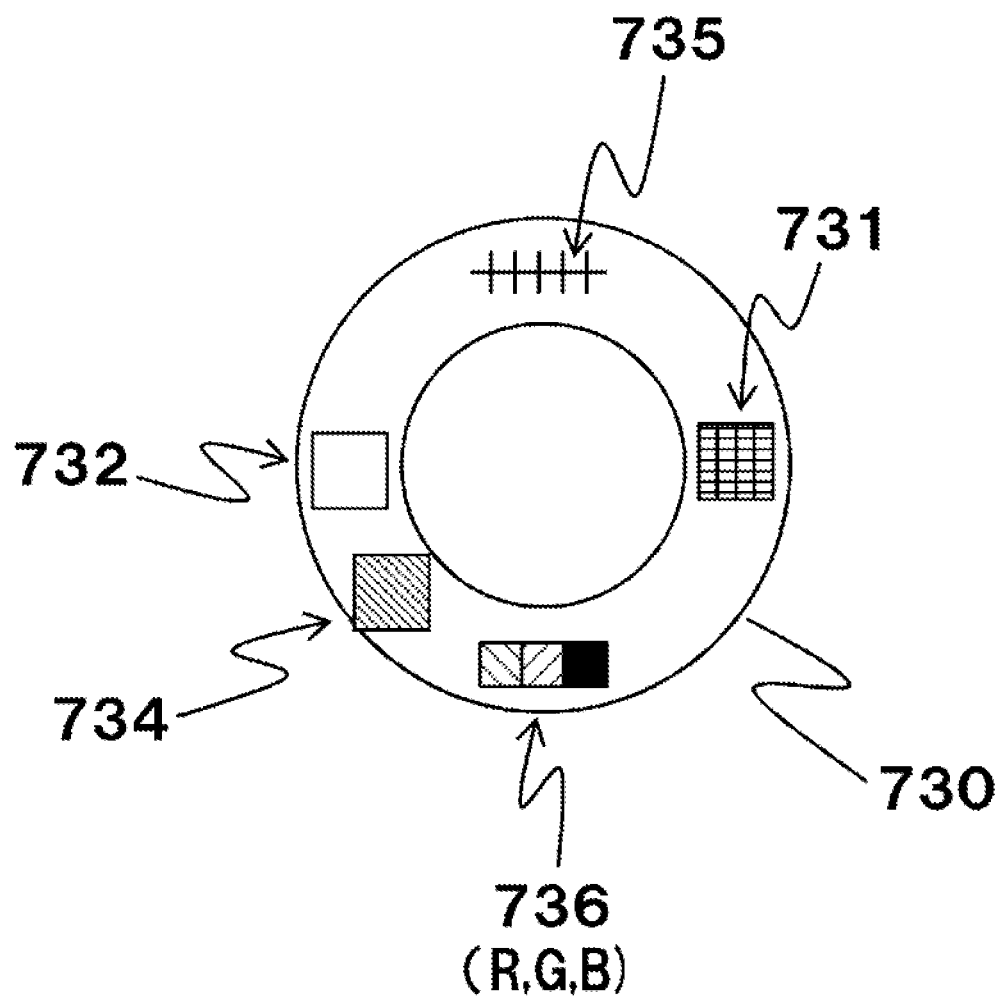
FIG. 34 is a diagram showing a modified example of a reference pattern.

FIGS. 34 to 37 show modified examples of a reference pattern. FIG. 34 shows an example of a case in which not only reference patterns for focus adjustment and reflectance correction but also a color adjustment pattern 736 (for example, a pattern of red R, green G and blue B) have been installed. By preparing the color adjustment pattern 736 in this way, it becomes possible to readily adjust a captured image with correct colors.

Figure 35:
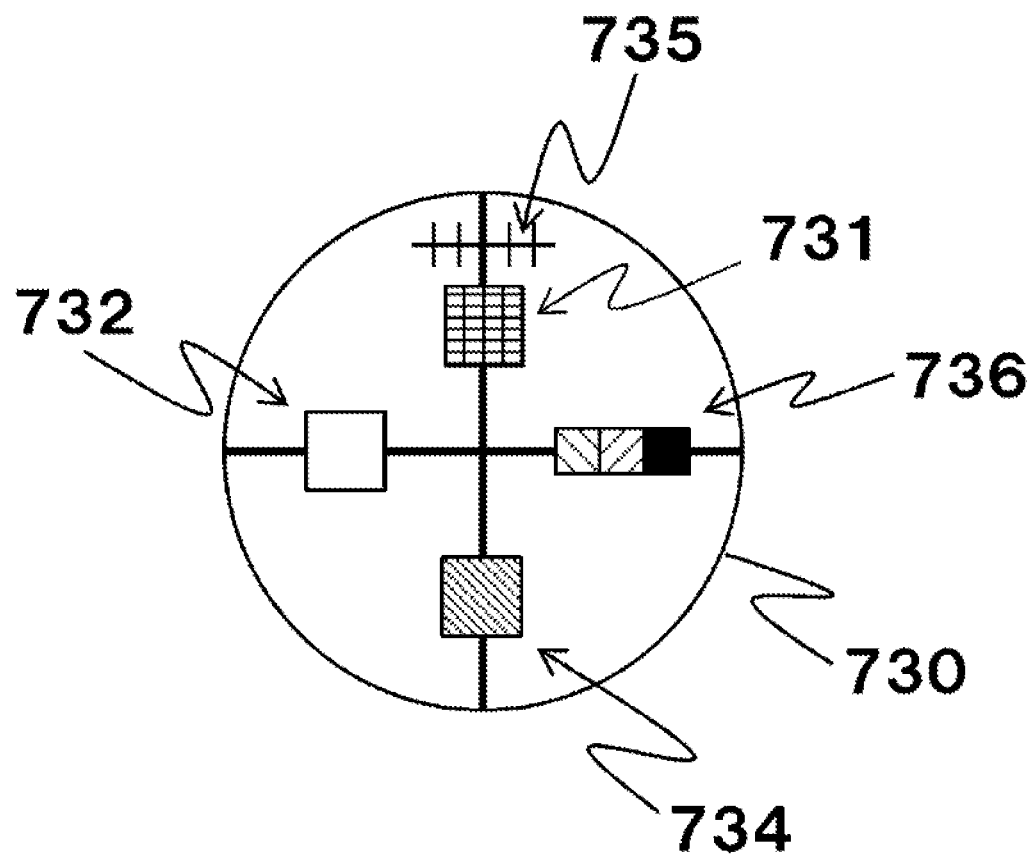
FIG. 35 is a diagram showing a modified example of a reference pattern.

FIG. 35 shows an example of a case in which reference patterns are placed on wires installed in a cross shape. In this way, an imaging region of a subject can be widened in comparison with FIG. 33 or FIG. 34. In other words, in the case shown in FIG. 33 or FIG. 34, a subject is hidden by a portion having a ring shape in which reference patterns are installed. However, when reference patterns are placed on wires installed in a cross shape, a portion in which a subject is hidden can be reduced.

Figure 36:
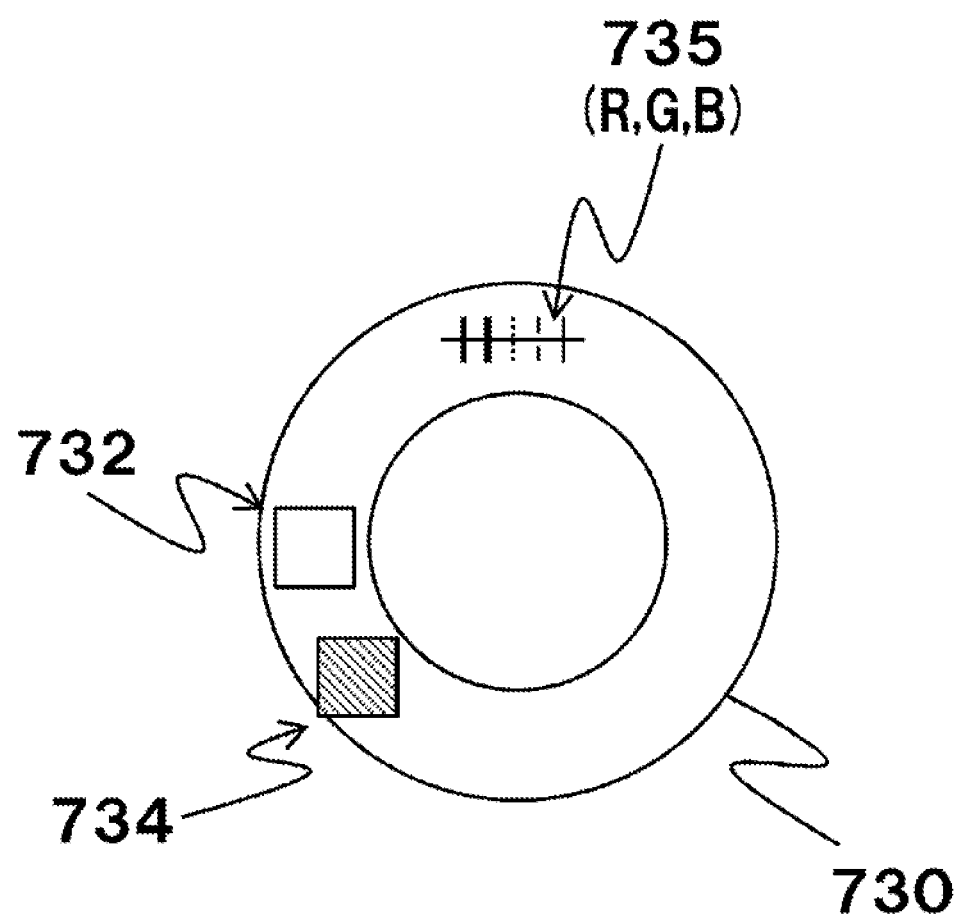
FIG. 36 is a diagram showing a modified example of a reference pattern.

FIG. 36 shows an example of a case in which the pattern 735 for checking a subject size is enabled to display a plurality colors (for example, a pattern of red R, green G and blue B). In this way, when the pattern 735 for checking a subject size is enabled to display a plurality of colors, it is possible to readily adjust a captured image with correct colors using the pattern 735 for checking a subject size.

Figure 37:
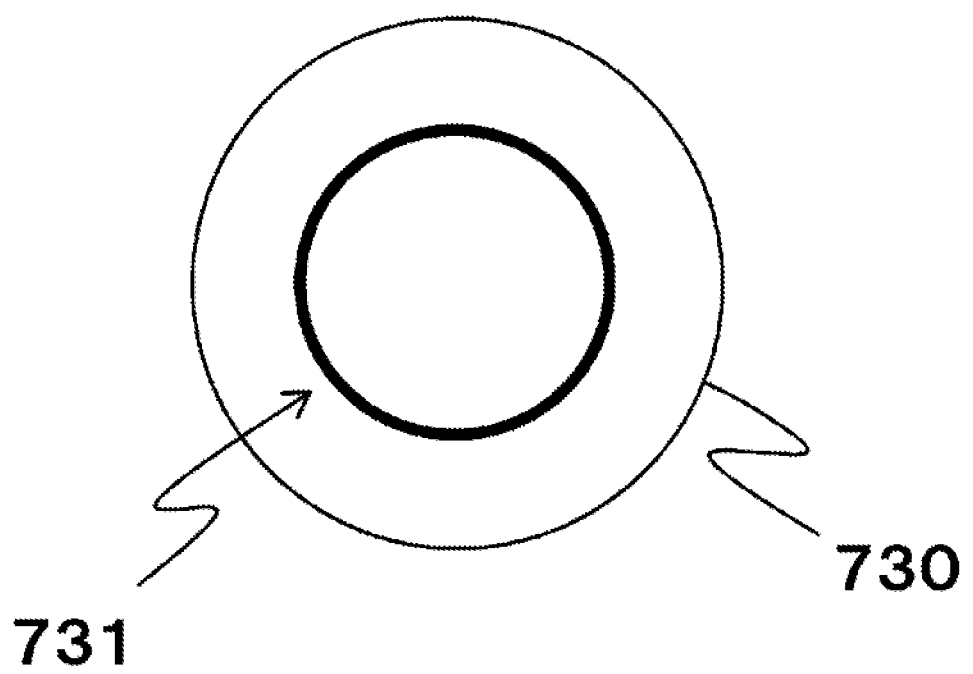
FIG. 37 is a diagram showing a modified example of a reference pattern.

FIG. 37 shows an example of a case in which the focus adjustment pattern 731 is configured by drawing a high-contrast line along the boundary between a subject region and a reference pattern region.

Figure 38:
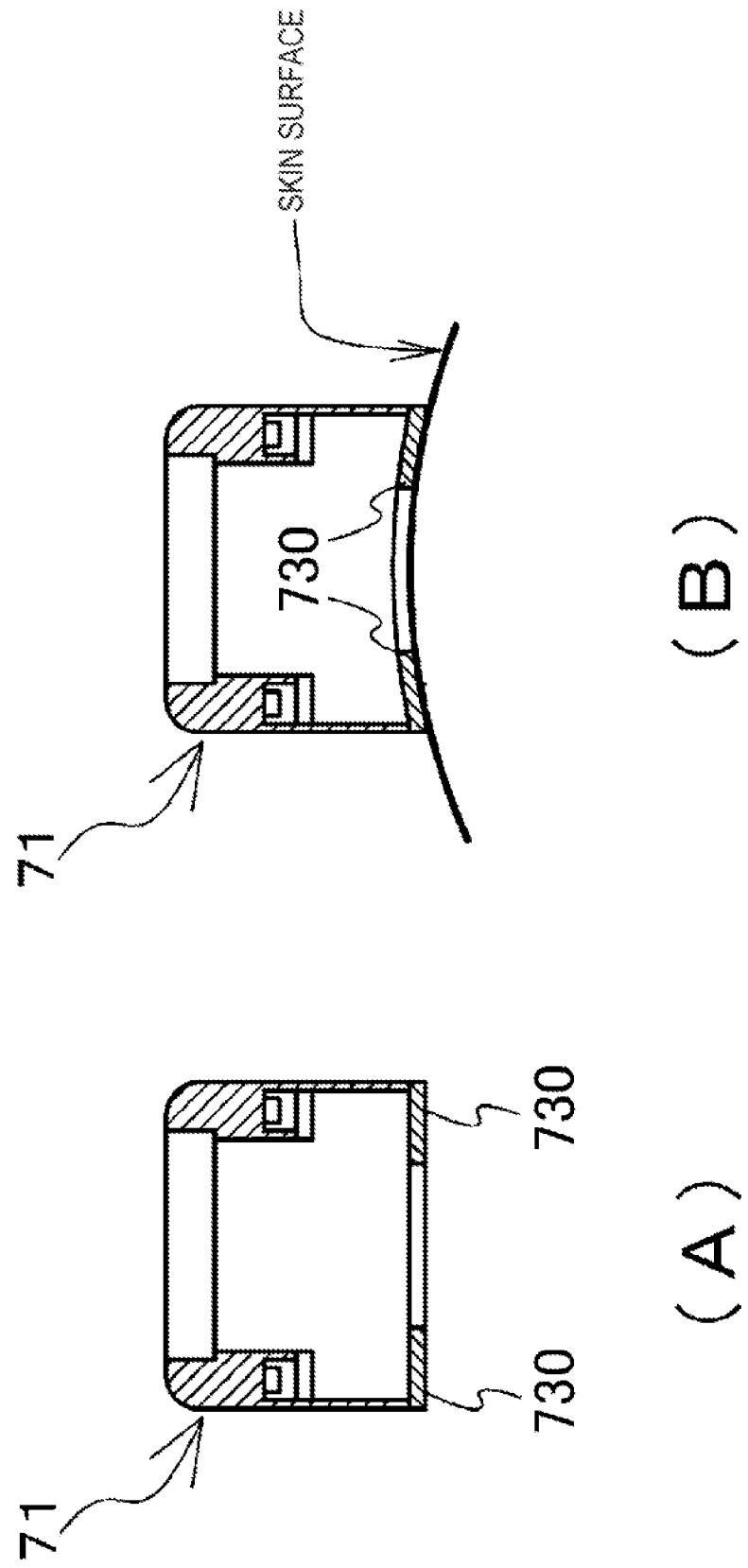
FIG. 38 is a diagram showing a case in which a reference pattern is formed on a flexible member.

Furthermore, in the reference pattern unit 730, reference patterns may be formed on a solid material such as metal, plastic, or the like, and as shown in FIG. 38, reference patterns may be formed on a flexible member, for example, a sheet, a film, or the like. When reference patterns are formed on a flexible member, as shown in FIG. 38(B), the reference patterns can closely contact with a subject (skin).

The imaging device 20 has the imaging optical system 22 that can capture a measurement target in a sufficient size at an angle of view at which it is possible to capture reference patterns and a subject region, and the image sensor 25 having a number of pixels capable of capturing with a sufficient resolution. For example, when the imaging optical system 22 having a magnification of about 50 times is used, it is preferred that the image sensor 25 have about 1,300,000 pixels. Also, when a zoom function is included in the imaging optical system 22, a wide angle is used to capture reference patterns, and a telescopic side is used to capture a subject, so that a subject can be measured more minutely. When a fixed focus optical system is included, it is preferable to design and set an angle of view and the like of the imaging optical system in advance so that reference patterns and a subject region are sufficiently shown in the field of vision.

3-2. Operation of Imaging Device

Figure 39:
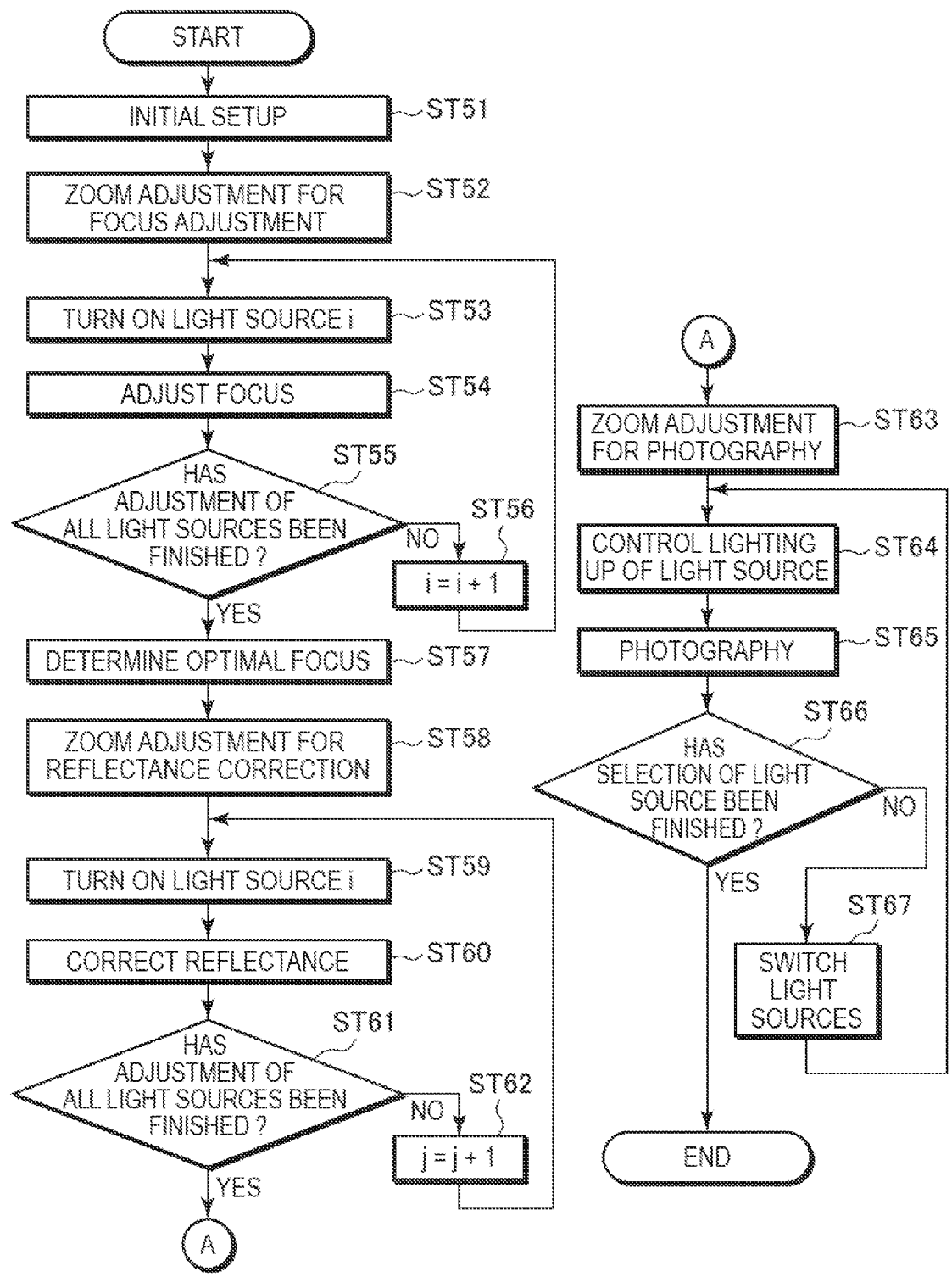
FIG. 39 is a flowchart illustrating operation of an imaging device.

FIG. 39 is a flowchart illustrating operation of an imaging device. In step ST51, the imaging device 20 performs initial setup. The imaging device 20 sets a parameter "i" indicating a light source that will be turned on as, for example, "i=1." Also, the imaging device 20 sets a parameter "j" indicating a light source that will be turned on to correct a reflectance as, for example, "j=1," and the process proceeds to step ST52.

In step ST52, the imaging device 20 performs zoom adjustment for focus control. The imaging device 20 controls the imaging optical system 22 so that the focus adjustment pattern 731 comes in the field of vision, and a sufficient region to perform focus control is shown, and the process proceeds to step ST53.

In step ST53, the imaging device 20 turns on a light source i, and the process proceeds to step ST54.

In step ST54, the imaging device 20 performs focus adjustment. Based on a captured image generated by an image sensor, the imaging device 20 performs focus adjustment. Also, the imaging device 20 calculates evaluation values indicating focus states, and the process proceeds to step ST55.

In step ST55, the imaging device 20 determines whether adjustment has been performed on all light sources. For example, when n light sources having different lighting directions are installed, the imaging device 20 determines that adjustment has been performed on all the light sources in the case of i=n, and the process proceeds to step. In the case of i<n, the imaging device 20 determines that adjustment of all the light sources has not been finished, and the process proceeds to step ST56

In step ST56, the imaging device 20 performs an arithmetic operation of "i=i+1" to update the parameter i, and the process returns to step ST53.

In step, the imaging device 20 determines optimal focus. Based on the evaluation values calculated according to the respective lighting directions, the imaging device 20 determines a lighting direction in which a focus state becomes best, and the process proceeds to step ST58.

In step ST58, the imaging device 20 performs zoom adjustment for reflectance correction. The imaging device 20 controls the imaging optical system 22 so that the reflectance correction patterns 732 to 734 and the like come in the field of vision, and the process proceeds to step ST59.

In step ST59, the imaging device 20 turns on a light source j, and the process proceeds to step ST60.

In step ST60, the imaging device 20 performs reflectance correction. When the light source j is a white LED that is a light source for correcting a visible light reflectance, the imaging device 20 performs configuration using imaging results of a pattern for correcting a visible light reflectance. For example, when a pixel value of a captured image of a white region is higher than a predetermined level, the imaging device 20 reduces the quantity of light and captures again. When a pixel value of a captured image of the pattern for correcting a visible light reflectance is in a predetermined level range, the imaging device 20 stores the pixel value and a light emission control value of this time. When a white region is captured, but it is not possible to obtain a captured image of desired brightness even with the maximum quantity of light, the imaging device 20 increases a gain of the image sensor 25 to obtain a captured image of the desired brightness, and stores the gain of this time. Also the imaging device 20 performs reflectance correction using other light sources and patterns for reflectance correction. Furthermore, the imaging device 20 may obtain a black offset value from a captured image of a black region, store the black offset value, subtract the black offset value from a pixel value of the captured image, and use the calculated value in the subsequent process.

Figure 40:
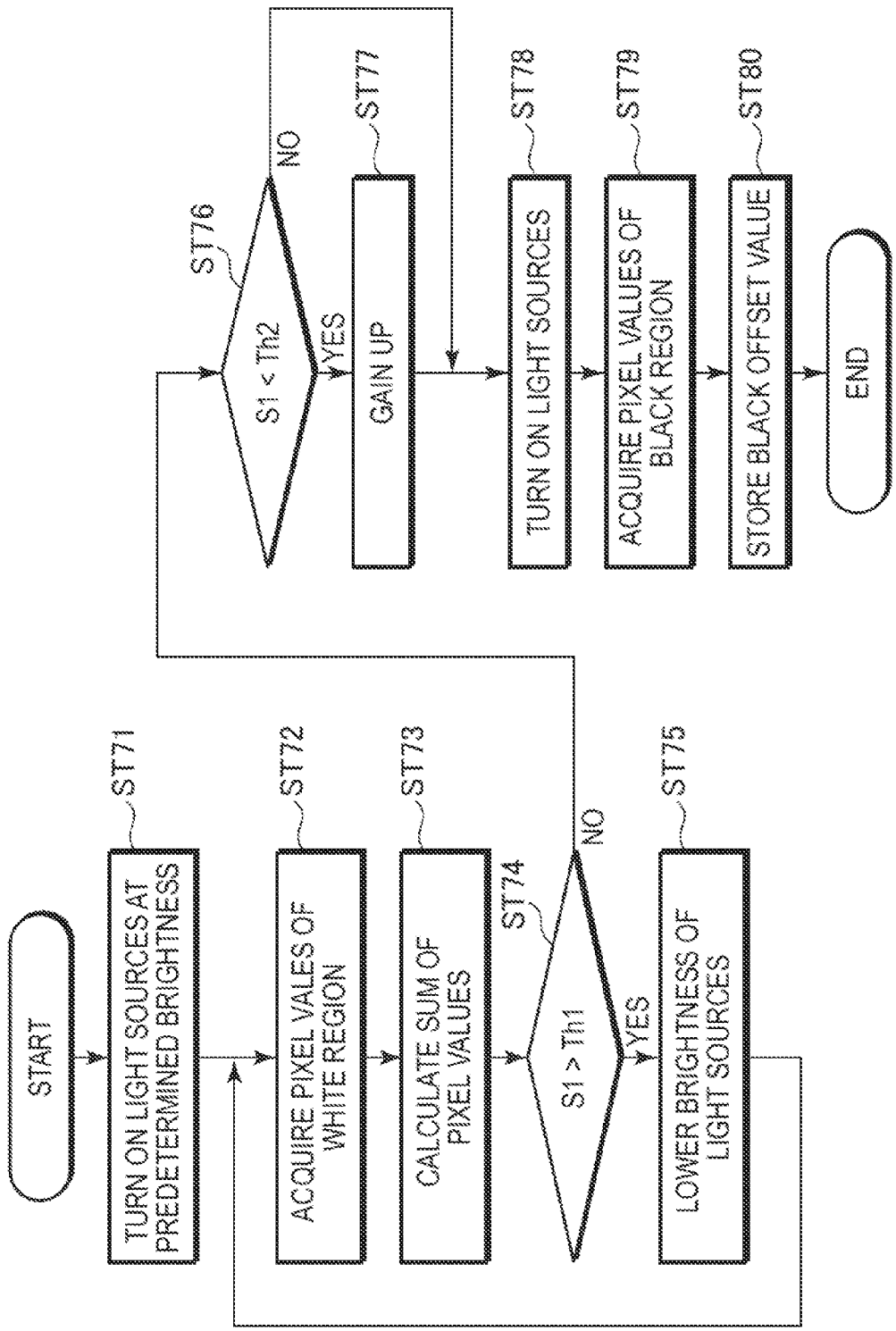
FIG. 40 is a flowchart illustrating operation of a correction process.

FIG. 40 illustrates an example of operation of a correction process using a white region and a black region. In step ST71, the imaging device 20 turns on light sources at a predetermined brightness. The imaging device 20 turns on, for example, white LEDs at the predetermined brightness, and the process proceeds to step ST72.

In step ST72, the imaging device 20 acquires pixel values of a white region. The imaging device 20 acquires pixel values of respective pixels in the white region of a pattern for correcting a visible light reflectance, and the process proceeds to step ST73.

In step ST73, the imaging device 20 calculates the sum of the pixel values. The imaging device 20 calculates the sum (S1) of the pixel values acquired in step ST72, and the process proceeds to step ST73.

In step ST74, the imaging device 20 determines whether the sum (S1) of the pixel values is larger than a threshold value (Th1). The process of the imaging device 20 proceeds to step ST75 when the sum (S1) of the pixel values is larger than the threshold value (Th1), and the process proceeds to step ST76 when the sum (S1) of the pixel values is equal to or smaller than the threshold value (Th1).

In step ST75, the imaging device 20 lowers the brightness of the light sources. Since the brightness of a captured image of the white region is higher than a predetermined level, the imaging device 20 lowers the brightness of the white LEDs, and the process returns to step ST72.

In step ST76, the imaging device 20 determines whether the sum (S1) of the pixel values is smaller than a threshold value (Th2). The process of the imaging device 20 proceeds to step ST77 when the sum (S1) of the pixel values is smaller than the threshold value (Th2), and the process proceeds to step ST78 when the sum (S1) of the pixel values is equal to or greater than the threshold value (Th2).

In step ST77, the imaging device 20 increases a gain of an image sensor. Since the brightness of the captured image of the white region is darker than a predetermined level, the imaging device 20 increases the gain of the image sensor 25, and the process proceeds back to step ST72.

In step ST78, the imaging device 20 turns on light sources, and the process proceeds to step ST79.

In step ST79, the imaging device 20 acquires pixels values of a black region. The imaging device 20 acquires pixel values of respective pixels in the black region of a pattern for correcting a visible light reflectance, and the process proceeds to step ST80.

In step ST80, the imaging device 20 stores a black offset value. The imaging device 20 sets a black offset value from the pixel values of the respective pixels of the black region acquired in step ST79. For example, the imaging device stores an average of the pixel values of the respective pixels in the black region as a black offset value. In this way, the imaging device 20 performs reflectance correction.

In step ST61 of FIG. 39, the imaging device 20 determines whether adjustment has been performed on all the light sources. For example, when q light sources having different wavelengths are installed so as to perform a plurality of types of correction, the imaging device 20 determines that adjustment has been performed on all the light sources in the case of i=q, and the process proceeds to step ST63. In the case of i<q, the imaging device 20 determines that adjustment has not been performed on all the light sources, and the process proceeds to step ST62.

In step ST62, the imaging device 20 performs an arithmetic operation of "j=j+1" to update the parameter j, and the process returns to step ST59.

In step ST63, the imaging device 20 performs zoom adjustment for capturing. The imaging device 20 controls the imaging optical system 22 so that the whole field of vision is filled with a subject region as an optimal focus state, and the process proceeds to step ST64.

In step ST64, the imaging device 20 controls lighting up of a light source. The imaging device 20 selects a light source used in capturing, controls the quantity of emitted light based on a lighting-up control value for the selected light source, and the process proceeds to step ST65.

In step ST65, the imaging device 20 carries out photography. The imaging device 20 performs an imaging operation to acquire an image signal of a skin image, and the process proceeds to step ST66.

In step ST66, the imaging device 20 determines whether selection of a light source has been finished. The process of imaging device 20 proceeds to step ST67 when the capturing in which a light source having a desired wavelength is used has not been finished, and finishes the capturing when the capturing in which a light source having the desired wavelength is used has been finished, that is, selection of a light source has been finished.

In step ST67, the imaging device 20 switches light sources. Among light sources of the desired wavelength, the imaging device 20 selects a light source that has not yet been used in the capturing, and the process returns to step ST64.

When such a process is performed, in an optimal focus state, it is possible to readily obtain not only a captured image for which white light has been used as illumination light but also a captured image of a case in which near infrared light, ultraviolet light, or the like has been used as illumination light. Also, without putting on and taking off a cap for reflectance correction, it is possible to automatically correct reflectance.

3-3. Another Configuration of Attachment Device

Figure 41:
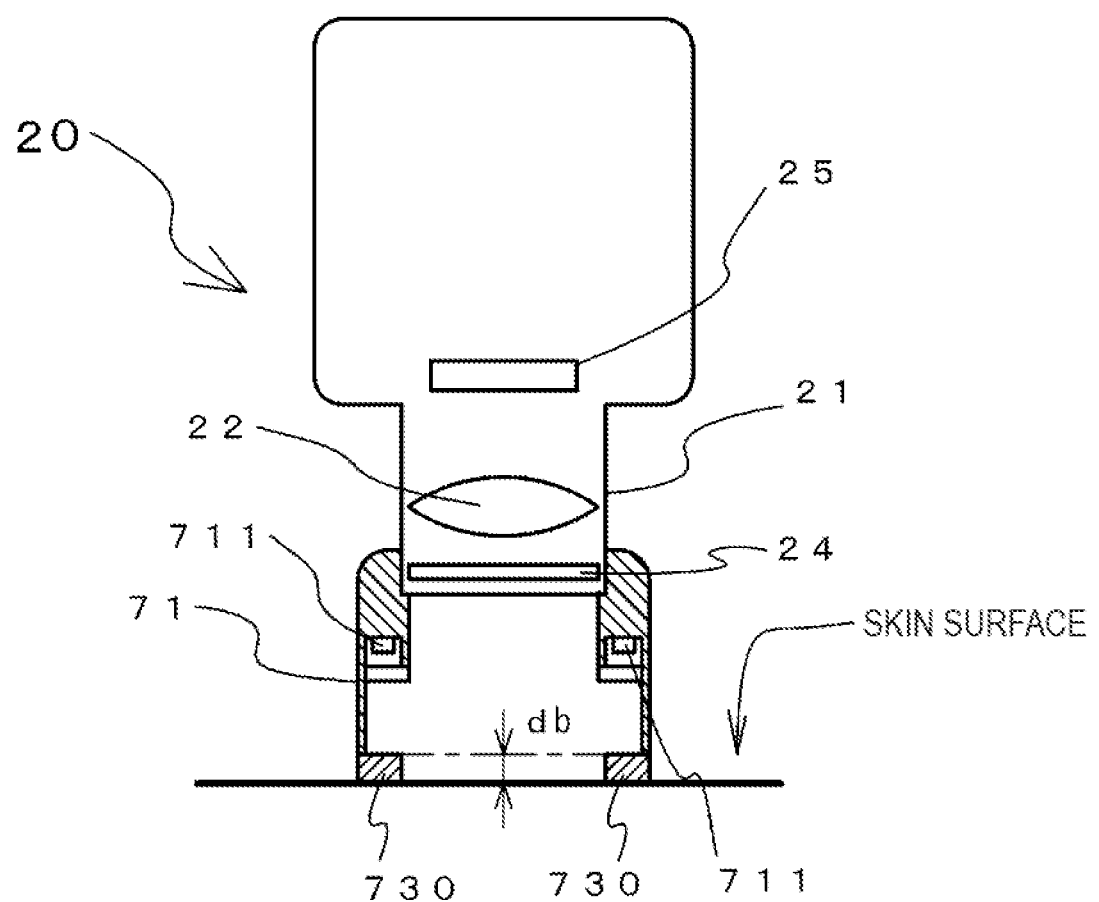
FIG. 41 is a diagram showing a case in which a reference pattern has a thick thickness.
Figure 42:
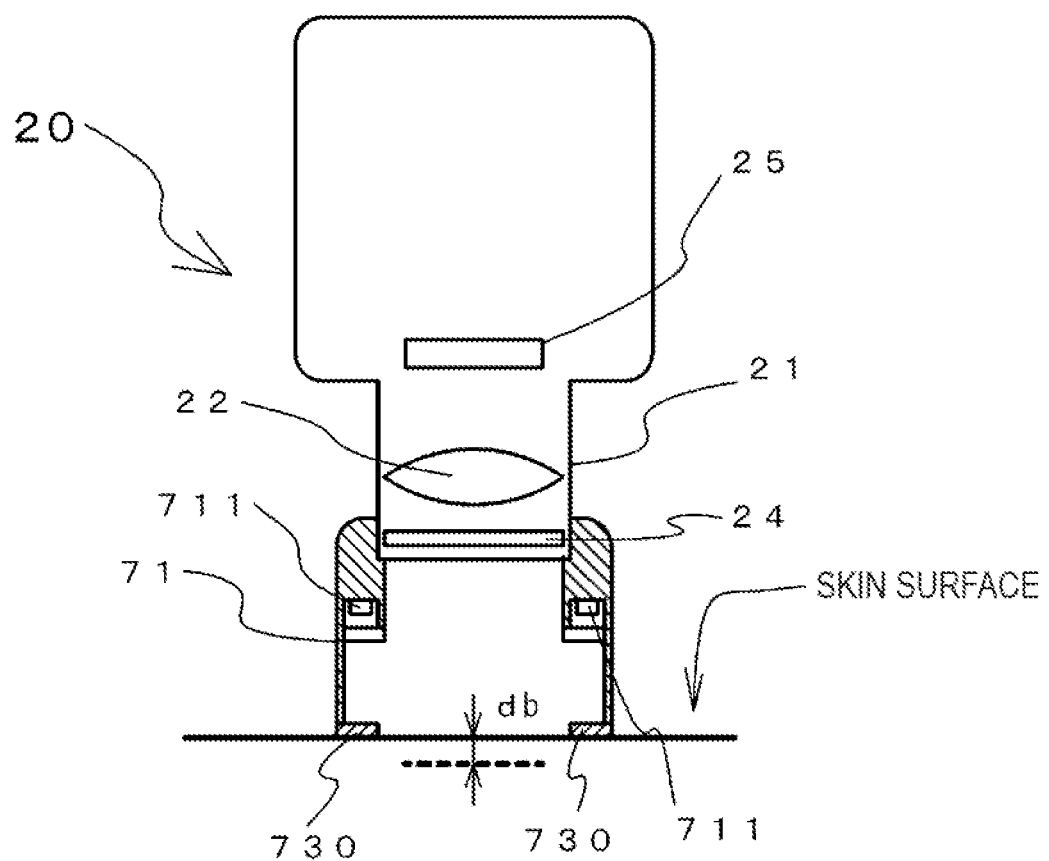
FIG. 42 is a diagram showing a case in which information is acquired by focusing on the inside of a subject.
Figure 43:
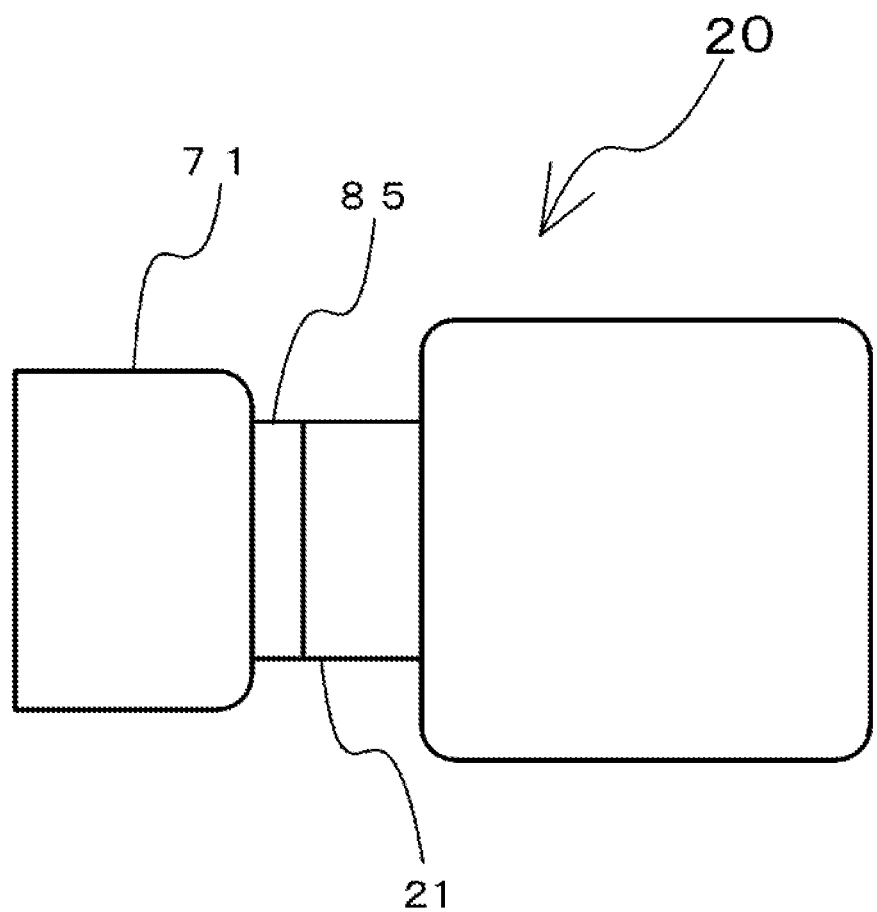
FIG. 43 is a diagram showing a configuration that connects a camera cone with an attachment device through an elastic body.

When a reference pattern has a thick thickness as shown in FIG. 41, there is a distance db between a pattern surface and a subject surface. Thus, there may be a case in which the pattern is in focus, but the subject surface is out of focus. By using a lens that has the depth of field in which both of the pattern surface and the subject surface are included, or adjusting focus as much as the pattern thickness (already known), it is preferable to focus on the subject surface. As shown in FIG. 42, by setting a lens or adjusting focus in the same way, it is also possible to focus on the inside of a subject as well as a surface of the subject and acquire information. As shown in FIG. 43, when the camera cone 21 and the attachment device 71 are configured to be connected through an elastic body 85, it is possible to adjust a force that presses the imaging device 20 against skin upon capturing of a skin image to be in a predetermined range. In this case, the distance between the imaging optical system 22 and a subject (for example, a skin surface) may change, but it becomes possible to correctly focus on the subject by using a pattern for focus control.

3-4. Regarding Image Processing Device and Display Device

As described above, using light sources having different wavelengths, an image signal of a captured image is generated in the imaging device 20. Also, by correcting reflectance, an image signal of the captured image is generated. Accordingly, an image processing device may perform skin analysis not only based on an image signal of the captured image for which a white light source has been used but also based on an image signal of the captured image for which a light source having a different wavelength has been used.

The analysis device 40 performs texture analysis using an image signal of the captured image that has been captured using a visible ray light source as described in, for example, the first embodiment. Also, the analysis device 40 conducts analysis of melanin using an image signal of a captured image that has been captured using, for example, a red light source or a near infrared light source. When a pixel value of a captured image that has been captured using a red light source is "Ired," and a pixel value of a captured image that has been captured using a near infrared light source is "IIR," an index of the amount of melanin (melanin index "MI") is calculated for each pixel based on equation (3).

$$MI = \frac{500}{\log 5}(\log I_{IR} - \log I_{red}) + 500 \quad (3)$$

In addition, an average value of a central region (for example, a region of 64×64 pixels) of each of the images may be obtained, and the respective average values may be used as "IIR" and "Ired" to calculate a melanin index of the images, Furthermore, it is also possible to analyze a skin condition using an evaluation value obtained by irradiating light in a plurality of directions so as to determine focus. For example, as described with reference to FIG. 22, an evaluation value becomes large when light is irradiated in a direction crossing wrinkles at right angles, and thus there are two peaks when a lighting direction is moved by 360 degrees. Meanwhile, if a shape of a skin bump of a portion in which wrinkles are not noticed is, for example, a quadrilateral shape, there are four peaks when a lighting direction is moved by 360 degrees. Based on this, a case in which there are two peaks may be determined as a state in which there are wrinkles, and rugosity may be determined based on a level of an evaluation value.

The display device 60 presents analysis results of the analysis device 40 to a user. For example, analysis results of texture or melanin are displayed as a graph, or a captured image displayed to be overlaid with a region of a high melanin index is presented to the user.

As described above, according to the second embodiment, it is possible to set the focus based on a reference pattern, and thus it becomes possible to appropriately and automatically set the focus even in a low contrast state such as a case of close-up imaging of skin, and the like. As a result, it is possible to improve the accuracy in measurement of fine texture of a skin surface and the like. In addition, correction of a reflectance can be automatically performed even without using a tool for reflectance correction, and thus inconvenience of correction for a user disappears. Furthermore, correction can be also automatically made at every skin measurement, and thus color measurement, spectral measurement, and the like become possible with higher accuracy.

Incidentally, a series of the processes described in the present specification can be executed by hardware, software, or a combination of both. The software can execute the processes by installing a program recording a processing sequence into a memory in a computer integrated with dedicated hardware, or by installing the program in a general purpose computer executable of various processes.

For example, the program can previously be recorded in a hard disk drive, ROM (Read Only Memory) or the like as a recording medium. Or the program can temporarily or permanently be stored (recorded) in a removable medium such as a flexible disk, CD-ROM (Compact Disc Read Only Memory), MO (Magneto optical) disk, DVD (Digital Versatile Disc), magnetic disk, semiconductor memory card. Such a removable recording medium can be provided as so-called packaged software.

Moreover, the program not only be installed in the computer form the removable recording medium but also may be installed by wireless or wired transferring into the computer via a network such as a LAN (Local Area Network) and the Internet from download sites. The computer can undergo installation of the received program, which is transferred like that, into the recording medium such as the mounted hard disk drive.

It should be understood by those skilled in the art that various modifications, combinations, sub-combinations and alterations may occur depending on design requirements and other factors insofar as they are within the scope of the appended claims or the equivalents thereof.

Additionally, the present technology may also be configured as below.

(1) An imaging device including:
  a lighting unit whose lighting directions to a subject are able to be switched; and
  a control unit that performs focus adjustment on the subject for every lighting directions to calculate evaluation values in accordance with focus states, and determines a direction in which a focus state becomes best as a lighting direction based on the evaluation values to capture the subject.

(2) The imaging device according to (1),
  wherein the lighting unit switches the lighting directions by emitting illumination light from different positions in a circumferential direction with respect to an optical axis of an imaging optical system.

(3) The imaging device according to (2),
  wherein the lighting unit switches irradiation angles of the illumination light.

(4) The imaging device according to (2) or (3),
  wherein the control unit thins out the lighting directions in the circumferential direction, performs focus adjustment on the subject for every lighting directions after thinning out to calculate evaluation values in accordance with focus states, and calculates evaluation values of the thinned-out lighting directions from the calculated evaluation values.

(5) The imaging device according to any one of (2) to (4),
  wherein the control unit groups the lighting directions in the circumferential direction, and performs focus adjustment on the subject for every lighting directions in one group to calculate evaluation values in accordance with focus states.

(6) The imaging device according to (5),
  wherein the control unit includes lighting directions crossing at right angles in the one group.

(7) The imaging device according to any one of (1) to (6),
  wherein the lighting unit provides lighting using a light source having an emission wavelength suitable for an analysis process performed using a captured image of the subject.

(8) The imaging device according to any one of (1) to (7),
  wherein the lighting unit switches the lighting directions by switching light sources emitting illumination light, or controlling passage of illumination light emitted from a light source using a shutter.

(9) The imaging device according to any one of (1) to (8),
  wherein the control unit moves a focus position by a predetermined distance with respect to a focus adjustment position at which the focus state becomes best based on the evaluation values.

In an imaging device, an imaging method, a program, an imaging system, and an attachment device of this technology, lighting directions of a subject can be switched. Thus, focus adjustment on a subject is performed for every lighting directions to calculate evaluation values in accordance with focus states, and a direction in which a focus state becomes best is determined as a lighting direction based on the evaluation values to capture the subject. For this reason, lighting is provided in an optimal direction to perform focus adjustment, and it becomes possible to readily obtain a skin image whose focus state is good. Accordingly, the imaging device, the imaging method, the program, the imaging system, and the attachment device are suitable for a system that captures a skin image or carries out skin analysis used in the beauty industry and the like.

What is claimed is:

1. An imaging device comprising:
a lighting unit configured to provide light to a subject from a direction obtained from a plurality of switchable lighting directions which are switchable therebetween; and
a control unit configured to perform focus adjustment on the subject for every one of more than one of the lighting directions to calculate evaluation values in accordance with focus states, and to determine a lighting direction to capture the subject which has an optimal focus state associated therewith as compared to the focus states based on the evaluation values.

2. The imaging device according to claim 1,
wherein the lighting unit switches the lighting directions by emitting illumination light from different positions in a circumferential direction with respect to an optical axis of an imaging optical system.

3. The imaging device according to claim 2,
wherein the lighting unit switches irradiation angles of the illumination light.

4. The imaging device according to claim 2,
wherein the control unit thins out the lighting directions in the circumferential direction, performs focus adjustment on the subject for every lighting directions after thinning out to calculate evaluation values in accordance with focus states, and calculates evaluation values of the thinned-out lighting directions from the calculated evaluation values.

5. The imaging device according to claim 2,
wherein the control unit groups the lighting directions in the circumferential direction, and performs focus adjustment on the subject for every lighting directions in one group to calculate evaluation values in accordance with focus states.

6. The imaging device according to claim 5,
wherein the control unit includes lighting directions crossing at right angles in the one group.

7. The imaging device according to claim 1,
wherein the lighting unit provides lighting using a light source having an emission wavelength suitable for an analysis process performed using a captured image of the subject.

8. The imaging device according to claim 1,
wherein the lighting unit switches the lighting directions by switching light sources emitting illumination light, or controlling passage of illumination light emitted from a light source using a shutter.

9. The imaging device according to claim 1,
wherein the control unit moves a focus position by a predetermined distance with respect to a focus adjustment position at which the focus state becomes best based on the evaluation values.

10. An imaging method comprising:
providing lighting to a subject from a direction obtained from a plurality of switchable lighting directions which are switchable therebetween; and
performing focus adjustment on the subject for every one of more than one of the lighting directions to calculate evaluation values in accordance with focus states, and to determine a lighting direction to capture the subject which has an optimal focus state associated therewith as compared to the focus states based on the evaluation values.

11. A non-transitory computer readable medium having stored thereon a program which when executed by a computer causes the computer to control operation of an imaging device having a lighting unit configured to provide light to a subject from a direction obtained from a plurality of switchable lighting directions which are switchable therebetween, and
to carry out a procedure of performing focus adjustment on the subject for every one of more than one of the lighting directions to calculate evaluation values in accordance with focus states, and to determine a lighting direction to capture the subject which has an optimal focus state associated therewith as compared to the focus states based on the evaluation values.

12. An imaging system comprising:
an imaging device that generates a captured image of a subject; and
an analysis device that analyzes the subject using the captured image,
wherein the imaging device includes
a lighting unit configured to provide light to a subject from a direction obtained from a plurality of switchable lighting directions which are switchable therebetween, and
a control unit configured to perform focus adjustment on the subject for every one of more than one of the lighting directions to calculate evaluation values in accordance with focus states, and to determine a lighting direction to capture the subject which has an optimal focus state associated therewith as compared to the focus states based on the evaluation values.

13. An attachment device comprising:
a lighting unit configured to provide light to a subject from a direction obtained from a plurality of switchable lighting directions which are switchable therebetween,
wherein the lighting unit is configured to automatically switch between at least a number of the lighting directions and output information pertaining thereto to an external device.

* * * * *